United States Patent
Li et al.

(10) Patent No.: US 10,100,360 B2
(45) Date of Patent: Oct. 16, 2018

(54) BIOMARKERS FOR DIABETES AND USAGES THEREOF

(71) Applicants: BGI SHENZHEN, Shenzhen, Guangdong (CN); BGI SHENZHEN CO., LIMITED, Shenzhen, Guangdong (CN)

(72) Inventors: Shenghui Li, Shenzhen (CN); Qiang Feng, Shenzhen (CN); Zhuye Jie, Shenzhen (CN); Dongya Zhang, Shenzhen (CN); Junjie Qin, Shenzhen (CN); Jun Wang, Shenzhen (CN); Jian Wang, Shenzhen (CN); Huanming Yang, Shenzhen (CN)

(73) Assignees: BGI SHENZHEN, Shenzhen (CN); BGI SHENZHEN CO., LIMITED, Shenzhen (CN)

( * ) Notice: Subject to any disclaimer, the term of this patent is extended or adjusted under 35 U.S.C. 154(b) by 744 days.

(21) Appl. No.: 14/418,800

(22) PCT Filed: Jun. 5, 2013

(86) PCT No.: PCT/CN2013/076799
§ 371 (c)(1),
(2) Date: Jan. 30, 2015

(87) PCT Pub. No.: WO2014/019408
PCT Pub. Date: Feb. 6, 2014

(65) Prior Publication Data
US 2015/0292011 A1    Oct. 15, 2015

(30) Foreign Application Priority Data
Aug. 1, 2012  (WO) ................ PCT/CN2012/079497

(51) Int. Cl.
*C12Q 1/68* (2018.01)
*G06F 19/22* (2011.01)
(Continued)

(52) U.S. Cl.
CPC .......... *C12Q 1/6883* (2013.01); *G06F 19/22* (2013.01); *G16H 50/20* (2018.01);
(Continued)

(58) Field of Classification Search
None
See application file for complete search history.

(56) References Cited

U.S. PATENT DOCUMENTS

2011/0275079 A1   11/2011  Palma

FOREIGN PATENT DOCUMENTS

| CN | 101918589 A | 12/2010 | |
| WO | WO 2009064901 A2 * | 5/2009 | ........... C12Q 1/6883 |

OTHER PUBLICATIONS

International Search Report dated Sep. 12, 2013 in International Application PCT/CN2013/076799.
(Continued)

*Primary Examiner* — Kaijiang Zhang
(74) *Attorney, Agent, or Firm* — Pillsbury Winthrop Shaw Pittman LLP

(57) ABSTRACT

Biomarkers for diabetes and usages thereof are provided. And the biomarkers are nucleotides having polynucleotide sequences defined in SEQ ID NOs: 1-50.

3 Claims, 1 Drawing Sheet
Specification includes a Sequence Listing.

(51) Int. Cl.
  *G16H 50/20* (2018.01)
  *C12Q 1/6883* (2018.01)
(52) U.S. Cl.
  CPC .. *C12Q 2600/112* (2013.01); *C12Q 2600/156* (2013.01); *C12Q 2600/158* (2013.01)

(56) References Cited

OTHER PUBLICATIONS

Junjie Qin et al., A human gut microbial gene catalogue established by metagenomic sequencing, Mar. 4, 2010, Nature, vol. 464, No. 7285, pp. 59-67.
EMBL accession No. FP 236843.1, Jun. 22, 2010, EMBL database.
Manichanh C et al., Reduced diversity of faecal microbiota in Crohn's disease revealed by a metagenomic approach, Sep. 27, 2005, Inflammatory bowel disease, vol. 55, pp. 205-211.
Wei, Xiao et al., Research progress on the relationship between human intestinal microbiota and host diseases, Jan. 31, 2011, Chinese Journal of Microecology, vol. 23, No. 1, pp. 75-80.
Junjie Qin et al., A metagenome-wide association study of gut microbiota in type 2 diabetes, 2012, Nature, vol. 000.
Supplementary Information, Supplementary Methods, Sample collection and DNA extraction, www.nature.com/Nature 1, Oct. 4, 2012.

\* cited by examiner

BIOMARKERS FOR DIABETES AND USAGES THEREOF

CROSS-REFERENCE TO RELATED APPLICATION

The present application claims priority to and benefits of PCT application PCT/CN2013/076799 filed on Jun. 5, 2013, which in turn claims priority to PCT Application PCT/CN2012/079497, filed on Aug. 1, 2012, the entire contents of which are hereby incorporated by reference.

SEQUENCE LISTING

The instant application contains a Sequence Listing which has been submitted electronically in ASCII format and is hereby incorporated by reference in its entirety.

FIELD

The present disclosure relates to biomarkers, in particular to biomarkers for type II diabetes and usages thereof.

BACKGROUND

Type 2 Diabetes (T2D) which is a complex disorder influenced by both genetic and environmental components has become a major public health issue throughout the world. Currently, research to parse out the underlying genetic contributors to T2D is mainly through the use of genome-wide association studies (GWAS) focusing on identifying genetic components of the organism's genome. Recently, research has indicated that the risk of developing T2D may also involve factors from the 'other genome' that is—the 'intestinal microbiome' (also termed the 'gut metagenome').

Previous metagenomic research on the gut metagenome, primarily using 16S rRNA and whole-genome shotgun (WGS) sequencing, has provided an overall picture of commensal microbial communities and their functional repertoire, e.g., a catalogue of 3.3 million human gut microbial genes were established by MetaHIT consortium in 2010 and, of note, a more extensive catalogue of gut microorganisms and their genes were later published by the Human Microbiome Project Consortium.

However, more work is still required to understand T2D.

SUMMARY

Embodiments of the present disclosure seek to solve at least one of the problems existing in the prior art to at least some extent.

The present invention is based on the following findings by the inventors:

Assessment and characterization of gut microbiota has become a major research area in human disease, including Type 2 Diabetes (T2D), the most prevalent endocrine disease worldwide. To carry out analysis on gut microbial content in T2D patients, the inventors developed a protocol for a Metagenome-Wide Association Study (MGWAS) and undertook a two-stage MGWAS based on deep shotgun sequencing of the gut microbial DNA from 344 Chinese individuals. The inventors identified and validated ~60,000 T2D-associated markers. To exploit the potential ability of T2D classification by gut microbiota, the inventors developed a disease classifier system based on the 50 gene markers that defined as an optimal gene set by a minimum redundancy-maximum relevance (mRMR) feature selection method. For intuitive evaluation of the risk of T2D disease based on these 50 gut microbial gene markers, the inventors computed a healthy index. The inventors' data provide insight into the characteristics of the gut metagenome related to T2D risk, a paradigm for future studies of the pathophysiological role of the gut metagenome in other relevant disorders, and the potential usefulness for a gut-microbiota-based approach for assessment of individuals at risk of such disorders.

According to embodiments of a first broad aspect of the present disclosure, there is provided a set of isolated nucleic acid consisting of nucleotides having polynucleotide sequences defined in SEQ ID NOs: 1-50. Each isolated nucleic acid may be regarded as the biomarkers of animal's abnormal condition, for example, abnormal condition is Diabetes, optionally Type 2 Diabetes. Then the present disclosure also provides a further set of isolated nucleic acid consisting of nucleotides having at least one of polynucleotide sequences defined in SEQ ID NOs:1-50.

| Gene ID | Enrichment(1: T2D; 0: control) | SEQ ID NO: |
|---------|-------------------------------|------------|
| 71549   | 0 | 1  |
| 177161  | 0 | 2  |
| 190778  | 0 | 3  |
| 385329  | 0 | 4  |
| 416559  | 0 | 5  |
| 477895  | 1 | 6  |
| 1244332 | 1 | 7  |
| 1291357 | 1 | 8  |
| 1387335 | 1 | 9  |
| 1557502 | 0 | 10 |
| 1620316 | 1 | 11 |
| 1992076 | 1 | 12 |
| 2068775 | 0 | 13 |
| 2117152 | 0 | 14 |
| 2180264 | 0 | 15 |
| 2225866 | 1 | 16 |
| 2334913 | 1 | 17 |
| 2397550 | 0 | 18 |
| 2593669 | 1 | 19 |
| 2595597 | 1 | 20 |
| 2675015 | 0 | 21 |
| 2713042 | 1 | 22 |
| 2793768 | 1 | 23 |
| 2894876 | 0 | 24 |
| 3000934 | 1 | 25 |
| 3032499 | 1 | 26 |
| 3038272 | 1 | 27 |
| 3148324 | 1 | 28 |
| 3178766 | 1 | 29 |
| 3254222 | 1 | 30 |
| 3270078 | 0 | 31 |
| 3290036 | 0 | 32 |
| 3363465 | 1 | 33 |
| 3408481 | 0 | 34 |
| 3602416 | 1 | 35 |
| 3623578 | 0 | 36 |
| 3701064 | 1 | 37 |
| 3703189 | 0 | 38 |
| 3755200 | 0 | 39 |
| 3815632 | 0 | 40 |
| 3816960 | 0 | 41 |
| 3975901 | 0 | 42 |
| 4009880 | 0 | 43 |
| 4101102 | 0 | 44 |
| 4137796 | 0 | 45 |
| 4138030 | 0 | 46 |
| 4141152 | 0 | 47 |
| 4170120 | 1 | 48 |
| 4247778 | 0 | 49 |
| 4256783 | 0 | 50 |

Then, according to embodiments of a second broad aspect of the present disclosure, there is provided a method to determine abnormal condition in a subject comprising the step of determining presence or absence of nucleotides having polynucleotide sequences defined in SEQ ID NOs: 1-50 in a gut microbiota of the subject. Using this method, one may effectively determine whether a subject has abnormal condition.

According to the embodiments of present disclosure, the method to determine abnormal condition in a subject may further possess the following additional features:

According to one embodiment of present disclosure, the abnormal condition is Diabetes, optionally Type 2 Diabetes.

According to one embodiment of present disclosure, a excreta of the subject is assayed to determine the presence or absence of the nucleotides having polynucleotide sequences defined in SEQ ID NOs:1-50, optionally the excreta is a faecal sample.

According to one embodiment of present disclosure, determining the presence or absence of nucleotides having polynucleotide sequences defined in SEQ ID NOs:1-50 further comprises: isolating nucleic acid sample from the excreta of the subject; constructing a DNA library based on the obtaining nucleic acid sample; sequencing the DNA library to obtain a sequencing result; and determining the presence or absence of nucleotides having polynucleotide sequences defined in SEQ ID NOs:1-50, based on the sequencing result.

According to one embodiment of present disclosure, the sequencing step is conducted by means of next-generation sequencing method or next-next-generation sequencing method.

According to one embodiment of present disclosure, the s sequencing step is conducted by means of at least one apparatus selected from Hiseq 2000, SOLID, 454, and True Single Molecule Sequencing.

According to one embodiment of present disclosure, determining the presence or absence of nucleotides having polynucleotide sequences defined in SEQ ID NOs:1-50 further comprises: aligning the sequencing result against the nucleotides having polynucleotide sequences defined in SEQ ID NOs:1-50; and determining the presence or absence of the nucleotides having polynucleotide sequences defined in SEQ ID NOs:1-50 based on the alignment result.

According to one embodiment of present disclosure, the step of aligning is conducted by means of at least one of SOAP 2 and MAQ.

According to one embodiment of present disclosure, further comprising the steps of: determining relative abundances of nucleotides having polynucleotide sequences defined in SEQ ID NOs:1-50; and comparing the abundances with predicted critical values.

According to one embodiment of present disclosure, the presence of nucleotides having polynucleotide sequences defined in at least one of SEQ ID NOs: 6-9, 11-12, 16-17, 19-20, 22-23, 25-30, 33, 35, 37 and 48 or the absence of nucleotides having polynucleotide sequences defined in at least one of SEQ ID NOs: 1-5, 10, 13-15, 18, 21, 24, 31-32, 34, 36, 38-47 and 49-50 is an indication of abnormal condition, particularly Diabetes, more particularly Type 2 Diabetes.

According to one embodiment of present disclosure, the presence of nucleotides having polynucleotide sequences defined in at least one of SEQ ID NOs: 1-5, 10, 13-15, 18, 21, 24, 31-32, 34, 36, 38-47 and 49-50 or the absence of nucleotides having polynucleotide sequences defined in at least one of SEQ ID NOs: 6-9, 11-12, 16-17, 19-20, 22-23, 25-30, 33, 35, 37 and 48 is an indication of healthy subject, particularly on the terms of Diabetes, more particularly Type 2 Diabetes.

According to embodiments of a second broad aspect of the present disclosure, there is provided a method of determining abnormal condition in a subject comprising determine the relative abundance of biomarkers related to the abnormal condition. By means of the method, one may determine whether there is abnormal condition in the subject effectively, and the person skilled in the art may select the biomarker depending on the condition in interest, and the one may select the known biomarkers of the abnormal condition.

According to the embodiments of present disclosure, the method to determine abnormal condition in a subject may further possess the following additional features:

According to one embodiment of present disclosure, the abnormal condition is abnormal condition is Diabetes, optionally Type 2 Diabetes.

According to one embodiment of present disclosure, the biomarkers are nucleotides having polynucleotide sequences defined in at least one of SEQ ID NOs: 1-50 in a gut microbiota of the subject.

According to one embodiment of present disclosure, the presence of nucleotides having polynucleotide sequences defined in at least one of SEQ ID NOs: 6-9, 11-12, 16-17, 19-20, 22-23, 25-30, 33, 35, 37 and 48 or the absence of nucleotides having polynucleotide sequences defined in at least one of SEQ ID NOs: 1-5, 10, 13-15, 18, 21, 24, 31-32, 34, 36, 38-47 and 49-50 is an indication of Diabetes, more particularly Type 2 Diabetes.

According to one embodiment of present disclosure, the presence of nucleotides having polynucleotide sequences defined in at least one of SEQ ID NOs: 1-5, 10, 13-15, 18, 21, 24, 31-32, 34, 36, 38-47 and 49-50 or the absence of nucleotides having polynucleotide sequences defined in at least one of SEQ ID NOs: 6-9, 11-12, 16-17, 19-20, 22-23, 25-30, 33, 35, 37 and 48 is an indication of healthy subject, particularly on the terms of Diabetes, more particularly Type 2 Diabetes.

According to one embodiment of present disclosure, the relative abundances of nucleotides having polynucleotide sequences defined in at least one of SEQ ID NOs: 6-9, 11-12, 16-17, 19-20, 22-23, 25-30, 33, 35, 37 and 48 being above a predetermined critical value thereof or the relative abundance of nucleotides having polynucleotide sequences defined in at least one of SEQ ID NOs: 1-5, 10, 13-15, 18, 21, 24, 31-32, 34, 36, 38-47 and 49-50 being blow a predetermined critical value thereof, is an indication of Diabetes, more particularly Type 2 Diabetes.

According to one embodiment of present disclosure, the relative abundances of nucleotides having polynucleotide sequences defined in at least one of SEQ ID NOs: 1-5, 10, 13-15, 18, 21, 24, 31-32, 34, 36, 38-47 and 49-50 being above a predetermined critical value thereof or the relative abundance of nucleotides having polynucleotide sequences defined in at least one of SEQ ID NOs: 6-9, 11-12, 16-17, 19-20, 22-23, 25-30, 33, 35, 37 and 48 being blow a predetermined critical value thereof, is an indication of healthy subject, particularly on the terms of Diabetes, more particularly Type 2 Diabetes.

According to one embodiment of present disclosure, a gut healthy index is further determined based on the relative abundances of the nucleotides by the formula below:

$$I^d = \sum_{i \in N} A_i$$

$$I^n = \sum_{i \in M} A_i$$

$$I = \frac{I^d}{|N|} - \frac{I^n}{|M|}$$

wherein, $A_i$ is the relative abundance of marker i,

N is a subset of all patient-enriched markers in selected biomarkers related to the abnormal condition, M is a subset of all control-enriched markers in selected biomarkers related to the abnormal condition,

|N| and |M| are the biomarker number of these two sets, d represents that $I^d$ is calculated within a patient group, and n represents that $I^n$ is calculated within a control group.

According to embodiments of a forth broad aspect of the present disclosure, there is provided a system to assay abnormal condition in a subject comprising: nucleic acid sample isolation apparatus, which adapted to isolate nucleic acid sample from the subject; sequencing apparatus, which connected to the nucleic acid sample isolation apparatus and adapted to sequence the nucleic acid sample, to obtain a sequencing result; and alignment apparatus, which connect to the sequencing apparatus, and adapted to align the sequencing result against the nucleotides having polynucleotide sequences defined in SEQ ID NOs:1-50 in such a way that determine the presence or absence of the nucleotides having polynucleotide sequences defined in SEQ ID NOs: 1-50 based on the alignment result. By means the above system, one may conduct any previous method to assay abnormal condition, and then one may determine whether there is abnormal condition in the subject effectively.

According to the embodiments of present disclosure, the system to determine abnormal condition in a subject may further possess the following additional features:

According to one embodiment of present disclosure, the sequencing apparatus is adapted to carry out next-generation sequencing method or next-next-generation sequencing method.

According to one embodiment of present disclosure, sequencing apparatus is adapted to carry out at least one apparatus selected from Hiseq 2000, SOLID, 454, and True Single Molecule Sequencing.

According to one embodiment of present disclosure, the alignment apparatus is at least one of SOAP 2 and MAQ.

According to embodiments of a fifth broad aspect of the present disclosure, there is provided a system to assay abnormal condition in a subject comprising: means for isolating nucleic acid sample, which adapted to isolate nucleic acid sample from the subject; means for sequencing nucleic acid, which connected to the nucleic acid sample isolation apparatus and adapted to sequence the nucleic acid sample, to obtain a sequencing result; and means for alignment, which connect to the sequencing apparatus, and adapted to align the sequencing result against the nucleotides having polynucleotide sequences defined in SEQ ID NOs:1-50 in such a way that determine the presence or absence of the nucleotides having polynucleotide sequences defined in SEQ ID NOs:1-50 based on the alignment result. By means the above system, one may conduct any previous method to assay abnormal condition, and then one may determine whether there is abnormal condition in the subject effectively.

According to the embodiments of present disclosure, the system to determine abnormal condition in a subject may further possess the following additional features:

According to one embodiment of present disclosure, the sequencing apparatus is adapted to carry out next-generation sequencing method or next-next-generation sequencing method.

According to one embodiment of present disclosure, sequencing apparatus is adapted to carry out at least one apparatus selected from Hiseq 2000, SOLID, 454, and True Single Molecule Sequencing.

According to one embodiment of present disclosure, the alignment apparatus is at least one of SOAP 2 and MAQ.

According to embodiments of a sixth broad aspect of the present disclosure, there is provided a computer readable medium having computer instructions stored thereon for determining the relative abundance of biomarkers related to the abnormal condition. Using this computer readable medium one may determine whether there is abnormal condition in the subject effectively, and the person skilled in the art may select the biomarker depending on the condition in interest, and the one may select the known biomarkers of the abnormal condition.

According to the embodiments of present disclosure, the computer readable medium may further possess the following additional features:

According to one embodiment of present disclosure, the abnormal condition is abnormal condition is Diabetes, optionally Type 2 Diabetes.

According to one embodiment of present disclosure, the biomarkers are nucleotides having polynucleotide sequences defined in at least one of SEQ ID NOs: 1-50 in a gut microbiota of the subject.

According to one embodiment of present disclosure, the presence of nucleotides having polynucleotide sequences defined in at least one of SEQ ID NOs: 6-9, 11-12, 16-17, 19-20, 22-23, 25-30, 33, 35, 37 and 48 or the absence of nucleotides having polynucleotide sequences defined in at least one of SEQ ID NOs: 1-5, 10, 13-15, 18, 21, 24, 31-32, 34, 36, 38-47 and 49-50 is an indication of Diabetes, more particularly Type 2 Diabetes.

According to one embodiment of present disclosure, the presence of nucleotides having polynucleotide sequences defined in at least one of SEQ ID NOs: 1-5, 10, 13-15, 18, 21, 24, 31-32, 34, 36, 38-47 and 49-50 or the absence of nucleotides having polynucleotide sequences defined in at least one of SEQ ID NOs: 6-9, 11-12, 16-17, 19-20, 22-23, 25-30, 33, 35, 37 and 48 is an indication of healthy subject, particularly on the terms of Diabetes, more particularly Type 2 Diabetes.

According to one embodiment of present disclosure, the relative abundances of nucleotides having polynucleotide sequences defined in at least one of SEQ ID NOs: 6-9, 11-12, 16-17, 19-20, 22-23, 25-30, 33, 35, 37 and 48 being above a predetermined critical value thereof or the relative abundance of nucleotides having polynucleotide sequences defined in at least one of SEQ ID NOs: 1-5, 10, 13-15, 18, 21, 24, 31-32, 34, 36, 38-47 and 49-50 being blow a predetermined critical value thereof, is an indication of Diabetes, more particularly Type 2 Diabetes.

According to one embodiment of present disclosure, the relative abundances of nucleotides having polynucleotide sequences defined in at least one of SEQ ID NOs: 1-5, 10, 13-15, 18, 21, 24, 31-32, 34, 36, 38-47 and 49-50 being above a predetermined critical value thereof or the relative abundance of nucleotides having polynucleotide sequences defined in at least one of SEQ ID NOs: 6-9, 11-12, 16-17, 19-20, 22-23, 25-30, 33, 35, 37 and 48 being blow a predetermined critical value thereof, is an indication of healthy subject, particularly on the terms of Diabetes, more particularly Type 2 Diabetes.

According to one embodiment of present disclosure, a gut healthy index is further determined based on the relative abundances of the nucleotides by the formula below:

$$I^d = \sum_{i \in N} A_i$$

$$I^n = \sum_{i \in M} A_i$$

$$I = \frac{I^d}{|N|} - \frac{I^n}{|M|}$$

wherein,
$A_i$ is the relative abundance of marker i,
N is a subset of all patient-enriched markers in selected biomarkers related to the abnormal condition,
M is a subset of all control-enriched markers in selected biomarkers related to the abnormal condition,
|N| and |M| are the biomarker number of these two sets,
d represents that $I^d$ is calculated within a patient group, and
n represents that $I^n$ is calculated within a control group.

According to embodiments of a seventh broad aspect of the present disclosure, there is provided a usage of biomarkers as target for screening medicaments to treat or prevent abnormal conditions. In one embodiment the biomarkers are nucleotides having polynucleotide sequences defined in SEQ ID NOs:1-50, and the abnormal condition is Diabetes, optionally Type 2 Diabetes.

Additional aspects and advantages of embodiments of present disclosure will be given in part in the following descriptions, become apparent in part from the following descriptions, or be learned from the practice of the embodiments of the present disclosure.

BRIEF DESCRIPTION OF DRAWINGS

These and other aspects and advantages of the present disclosure will become apparent and more readily appreciated from the following descriptions taken in conjunction with the drawings, in which:

FIG. 1 shows a resulting curves or graphs according Example 1 and Example 2 of present disclosure. In which FIG. 1a shows that a classifier to identify T2D individuals was constructed using 50 gene markers selected by mRMR, and then, for each indivudal, a gut healthy index was calculated to evaluate the risk of T2D in Example 1. The histogram shows the distribution of gut healthy indexs for all individuals, in which values less than −1.5 and values greater than 3.5 were grouped. For each bin, the dots show the proportion of T2D patients in the population of that bin (y axis on the right). FIG. 1b show that the area under the ROC curve (AUC) of gut-microbiota-based T2D classification in Example 1. The black bars denote the 95% confidence interval (CI) and the area between the two outside curves represents the 95% CI shape. FIG. 1c shows that the gut healthy index was computed for an additional 11 Chinese T2D samples and 12 non-diabetic controls in Example 2. The box depicts the interquartile range (IQR) between the first and third quartiles (25th and 75th percentiles, respectively) and the line inside denotes the median, while the points represent the gut healthy index in each sample.

DETAILED DESCRIPTION

Figure 1:
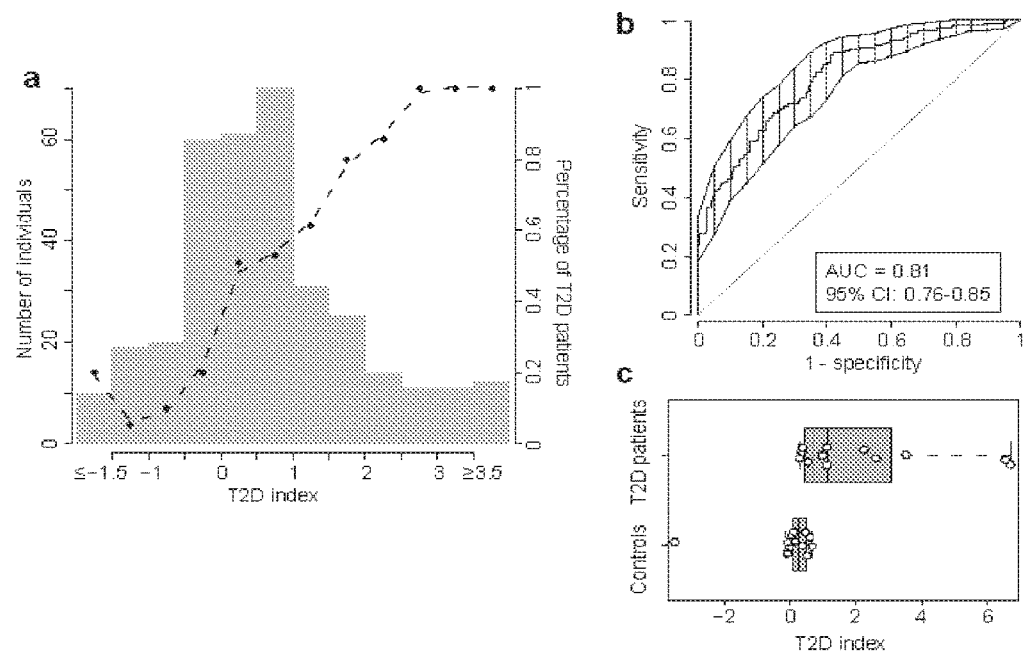

The present invention is further exemplified in the following non-limiting Examples. Unless otherwise stated, parts and percentages are by weight and degrees are Celsius. As apparent to one of ordinary skill in the art, these Examples, while indicating preferred embodiments of the invention, are given by way of illustration only, and the agents were all commercially available.

General Method

I. Methods for Detecting Biomarkers (Detect Biomarkers by Using a Two-Stage MGWAS)

To define T2D-associated metagenomic markers, the inventors devised and carried out a two-stage MGWAS strategy. Using a sequence-based profiling method, the inventors quantified the gut microbiota in samples for use in stage I. On average, with the requirement that there should be ≥90% identity, the inventors could uniquely map paired-end reads to the updated gene catalogue. To normalize the sequencing coverage, the inventors used relative abundance instead of the raw read count to quantify the gut microbial genes. The inventors then corrected for population stratification, which might be related to the non-T2D-related factors. For this the inventors analyzed our data using a modified EIGENSTRAT method (for detailed information, see Price, A. L. et al. Principal components analysis corrects for stratification in genome-wide association studies. *Nature genetics* 38, 904-909, doi:10.1038/ng1847 (2006), which is incoporated herein by reference); however, unlike what is done in a GWAS subpopulation correction, the inventors applied this analysis to microbial abundance rather than to genotype. A Wilcoxon rank-sum test was done on the adjusted gene profile to identify differential metagenomic gene content between the T2D patients and controls. The outcome of our analyses showed a substantial enrichment of a set of microbial genes that had very small P values, as compared with the expected distribution under the null hypothesis, suggesting that these genes were true T2D-associated gut microbial genes.

To validate the significant associations identified in stage I, the inventors carried out stage II analysis using additional individuals. The inventors also used WGS sequencing in stage II. The inventors then assessed the stage I genes that had P values<0.05 in these stage II study samples. The inventors next controlled for the false discovery rate (FDR) in the stage II analysis, and defined T2D-associated gene markers from these genes corresponding to a FDR (Stage II P value<0.01).

II. Methods for Selecting 50 Best Markers from Biomarkers

To defined an optimal gene set, a minimum redundancy-maximum relevance (mRMR) (for detailed information, see Peng, H., Long, F. & Ding, C. Feature selection based on mutual information: criteria of max-dependency, max-relevance, and min-redundancy. *IEEE Trans Pattern Anal Mach Intell* 27, 1226-1238, doi:10.1109/TPAMI.2005.159 (2005), which is incorporated herein by reference) feature selection method was used to select from all the T2D-associated gene markers. Fifty optimal gene markers were obtained as shown on Table 1.

TABLE 1

50 optimal Gene markers' enrichment

| Gene ID | Enrichment(1: T2D; 0: control) | SEQ ID NO: |
|---|---|---|
| 71549 | 0 | 1 |
| 177161 | 0 | 2 |
| 190778 | 0 | 3 |
| 385329 | 0 | 4 |
| 416559 | 0 | 5 |
| 477895 | 1 | 6 |
| 1244332 | 1 | 7 |
| 1291357 | 1 | 8 |
| 1387335 | 1 | 9 |
| 1557502 | 0 | 10 |
| 1620316 | 1 | 11 |
| 1992076 | 1 | 12 |
| 2068775 | 0 | 13 |
| 2117152 | 0 | 14 |
| 2180264 | 0 | 15 |
| 2225866 | 1 | 16 |
| 2334913 | 1 | 17 |
| 2397550 | 0 | 18 |
| 2593669 | 1 | 19 |
| 2595597 | 1 | 20 |
| 2675015 | 0 | 21 |
| 2713042 | 1 | 22 |
| 2793768 | 1 | 23 |
| 2894876 | 0 | 24 |
| 3000934 | 1 | 25 |
| 3032499 | 1 | 26 |
| 3038272 | 1 | 27 |
| 3148324 | 1 | 28 |
| 3178766 | 1 | 29 |
| 3254222 | 1 | 30 |
| 3270078 | 0 | 31 |
| 3290036 | 0 | 32 |
| 3363465 | 1 | 33 |
| 3408481 | 0 | 34 |
| 3602416 | 1 | 35 |
| 3623578 | 0 | 36 |
| 3701064 | 1 | 37 |
| 3703189 | 0 | 38 |
| 3755200 | 0 | 39 |
| 3815632 | 0 | 40 |
| 3816960 | 0 | 41 |
| 3975901 | 0 | 42 |
| 4009880 | 0 | 43 |
| 4101102 | 0 | 44 |
| 4137796 | 0 | 45 |
| 4138030 | 0 | 46 |
| 4141152 | 0 | 47 |
| 4170120 | 1 | 48 |
| 4247778 | 0 | 49 |
| 4256783 | 0 | 50 |

III Gut Healthy Index

To exploit the potential ability of Disease classification by gut microbiota, the inventors developed a Disease classifier system based on the gene markers that the inventors defined. For intuitive evaluation of the risk of disease based on these gut microbial gene markers, the inventors computed a gut healthy index.

To evaluate the effect of the gut metagenome on T2D, the inventors defined and computed the gut healthy index for each individual on the basis of the selected 50 gut metagenomic markers by mRMR method. For each individual sample, the gut healthy index of sample j that denoted by $I_j$ was computed by the formula below:

$$I_j^d = \sum_{i \in N} A_{ij}$$

$$I_j^n = \sum_{i \in M} A_{ij}$$

$$I_j = \frac{I_j^d}{|N|} - \frac{I_j^n}{|M|}$$

$A_{ij}$ is the relative abundance of marker i in sample j.

N is a subset of all patient-enriched markers in selected biomarkers related to the abnormal condition, M is a subset of all control-enriched markers in selected biomarkers related to the abnormal condition,

|N| and |M| are the biomarker number of these two sets, d represents that $I^d$ is calculated within a patient group, and n represents that $I^n$ is calculated within a control group.

IV Disease Classifier System

After identifying biomarkers from two stage MWAS strategy, the inventors, in the principle of biomarkers used to classify should be strongest to the classification between disease and healthy with the least redundancy, rank the biomarkers by a minimum redundancy-maximum relevance (mRMR) and find a sequential markers sets (its size can be as large as biomarkers number). For each sequential set, the inventors estimated the error rate by a leave-one-out cross-validation (LOOCV) of a classifier (such as logistic regression). The optimal selection of marker sets was the one corresponding to the lowest error rate (In some embodiments, the inventors have selected 50 biomarkers).

Finally, for intuitive evaluation of the risk of disease based on these gut microbial gene markers, the inventors computed a gut healthy index. Larger the healthy index, bigger the risk of disease. Smaller the healthy index, more healthy the people. The inventors can build a optimal healthy index cutoff based on a large cohort. If the test sample healthy index is bigger than the cutoff, then the person is in bigger disease risk. And if the test sample healthy index is smaller than the cutoff then he is more healthy. The optimal healthy index cutoff can be determined by a ROC method when the sum of the sensitivity and specificity reach at its maximal.

Example 1 Identify 50 Biomarker from 344 Chinese Individuals and Use Gut Healthy Index to Evaluate their T2D Risk Sample Collection and DNA Extraction All 344 faecal samples from 344 Chinese individuals living in the south of China, were collected by three local hospitals, such as Shenzhen Second People's Hospital, Shenzhen Hospital of Peking University and Medical Research Center of Guangdong General Hospital, including 344 samples for MWAS. The patients who were diagnosed with type 2 Diabetes Mellitus according to the 1999 WHO criteria (Alberti, K. G & Zimmet, P. Z. Definition, diagnosis and classification of diabetes mellitus and its complications. Part 1: diagnosis and classification of diabetes mellitus provisional report of a WHO consultation. Diabetic medicine: a journal of the British Diabetic Association 15, 539-553, doi:10.1002/(SICI)1096-9136(199807)15:7<539:: AID-DIA668>3.0.CO; 2-S (1998), incorporated herein by reference) constitute the case group in our study, and the rest non-diabetic individuals were taken as the control group (Table 2). Patients and healthy controls were asked to provide a frozen faecal sample. Fresh faecal samples were obtained at home, and samples were immediately frozen by storing in a home freezer. Frozen samples were transferred to BGI-Shenzhen, and then stored at −80° C. until analysis.

A frozen aliquot (200 mg) of each fecal sample was suspended in 250 μl of guanidine thiocyanate, 0.1 M Tris (pH 7.5) and 40 μl of 10% N-lauroyl sarcosine. DNA was extracted as previously described (Manichanh, C. et al. Reduced diversity of faecal microbiota in Crohn's disease revealed by a metagenomic approach. Gut55, 205-211, doi:gut.2005.073817 [pii]10.1136/gut.2005.073817 (2006), incorporated herein by reference). DNA concentration and molecular size were estimated using a nanodrop instrument (Thermo Scientific) and agarose gel electrophoresis.

TABLE 2

Sample collection

| Sample | T2D | Obese | samples | |
|--------|-----|-------|---------|---------|
|        |     |       | StageI  | StageII |
| DO     | Y   | Y     | 32      | 73      |
| DL     | Y   | N     | 39      | 26      |
| NO     | N   | Y     | 37      | 62      |
| NL     | N   | N     | 37      | 38      |

DNA Library Construction and Sequencing

DNA library construction was performed following the manufacturer's instruction (Illumina). The inventors used the same workflow as described elsewhere to perform cluster generation, template hybridization, isothermal amplification, linearization, blocking and denaturation, and hybridization of the sequencing primers.

The inventors constructed one paired-end (PE) library with insert size of 350 bp for each samples, followed by a high-throughput sequencing to obtain around 20 million PE reads. The reads length for each end is 75 bp-100 bp (75 bp and 90 bp read length in stage I samples; 100 bp read length for stage II samples). High quality reads were extracted by filtering low quality reads with 'N' base, adapter contamination or human DNA contamination from the Illumina raw data. On average, the proportion of high quality reads in all samples was about 98.1%, and the actual insert size of our PE library ranges from 313 bp to 381 bp.

Construction of a Gut Metagenome Reference

To identify metagenomic markers associated with T2D, the inventors first developed a comprehensive metagenome reference gene set that included genetic information from Chinese individuals and T2D-specific gut microbiota, as the currently available metagenomic reference (the MetaHIT gene catalogue) did not include such data. The inventors carried out WGS sequencing on individual fecal DNA samples from 145 Chinese individuals (71 cases and 74 controls) and obtained an average of 2.61 Gb (15.8 million) paired-end reads for each, totaling 378.4 Gb of high-quality data that was free of human DNA and adapter contaminants. The inventors then performed de novo assembly and metagenomic gene prediction for all 145 samples. The inventors integrated these data with the MetaHIT gene catalogue, which contained 3.3 million genes (Qin, J. et al. A human gut microbial gene catalogue established by metagenomic sequencing. Nature 464, 59-65, doi:nature08821 [pii] 10.1038/nature08821 (2010), incorporated herein by reference) that were predicted from the gut metagenomes of individuals of European descent, and obtained an updated gene catalogue with 4,267,985 predicted genes. 1,090,889 of these genes were uniquely assembled from our Chinese samples, which contributed 10.8% additional coverage of sequencing reads when comparing our data against that from the MetaHIT gene catalogue alone.

Computation of Relative Gene Abundance.

The high quality reads from each sample were aligned against the gene catalogue using SOAP2 by the criterion of identity>90%. Only two types of mapping results were accepted: i). a paired-end read should be mapped onto a gene with the correct insert-size; ii). one end of the paired-end read should be mapped onto the end of a gene, assuming the other end of read was mapped outside the genic region. In both cases, the mapped read was only counted as one copy.

Then, for any sample S, the inventors calculated the abundance as follows:

Step 1: Calculation of the Copy Number of Each Gene:

$$b_i = \frac{x_i}{L_i}$$

Step 2: Calculation of the Relative Abundance of Gene:

$$a_i = \frac{b_i}{\Sigma_j b_j} = \frac{\frac{x_i}{L_i}}{\Sigma_j \frac{x_j}{L_j}}$$

$a_i$: The relative abundance of gene i in sample S.
$L_i$: The length of gene i.
$x_i$: The times which gene i can be detected in sample S (the number of mapped reads).
$b_i$: The copy number of gene i in the sequenced data from sample S.
$b_j$: The copy number of gene j in the sequenced data from sample S.

Estimation of Profiling Accuracy.

The inventors applied the method developed by Audic and Claverie (1997) (Audic, S. & Claverie, J. M. The significance of digital gene expression profiles. Genome Res7, 986-995 (1997), incorporated herein by reference) to assess the theoretical accuracy of the relative abundance estimates. Given that the inventors have observed $x_i$ reads from gene i, as it occupied only a small part of total reads in a sample, the distribution of $x_i$ is approximated well by a Poisson distribution. Let us denote N the total reads number in a sample, so $N=\Sigma_i x_i$. Suppose all genes are the same length, the relative abundance value $a_i$ of gene i simply is $a_i = x_i/N$. Then the inventors could estimate the expected probability of observing $y_i$ reads from the same gene i, is given by the formula below, $$P(a'_i \mid a_i) = P(y_i \mid x_i) = \frac{(x_i + y_i)!}{x_i! y_i! 2^{(x_i + y_i + 1)}}$$

Here, $a'_i = y_i/N$ is the relative abundance computed by $y_i$ reads (Audic, S. & Claverie, J. M. The significance of digital gene expression profiles. Genome Res7, 986-995 (1997), incorporated herein by reference). Based on this formula, the inventors then made a simulation by setting the value of $a_i$ from 0.0 to 1 e-5 and N from 0 to 40 million, in order to compute the 99% confidence interval for $a'_i$ and to further estimate the detection error rate.

Marker Identification Using a Two-Stage MGWAS

To define T2D-associated metagenomic markers, the inventors devised and carried out a two-stage MGWAS strategy. The inventors investigated the subpopulations of the 145 samples in these different profiles. The inventors then corrected for population stratification, which might be related to the non-T2D-related factors. For this the inventors analyzed our data using a modified EIGENSTRAT method (Price, A. L. et al. Principal components analysis corrects for stratification in genome-wide association studies. *Nature genetics* 38, 904-909, doi:10.1038/ng1847 (2006), incorporated herein by reference); however, unlike what is done in a GWAS subpopulation correction, the inventors applied this analysis to microbial abundance rather than to genotype. A Wilcoxon rank-sum test was done on the adjusted gene profile to identify differential metagenomic gene content between the T2D patients and controls. The outcome of our analyses showed a substantial enrichment of a set of microbial genes that had very small P values, as compared with the expected distribution under the null hypothesis, suggesting that these genes were true T2D-associated gut microbial genes. To validate the significant associations identified in stage I, the inventors carried out stage II analysis using an additional 199 Chinese individuals. The inventors also used WGS sequencing in stage II and generated a total of 830.8 Gb sequence data with 23.6 million paired-end reads on average per sample. The inventors then assessed the 278,167 stage I genes that had P values<0.05 and found that the majority of these genes still correlated with T2D in these stage II study samples. The inventors next controlled for the false discovery rate (FDR) in the stage II analysis, and defined a total of 52,484 T2D-associated gene markers from these genes corresponding to a FDR of 2.5% (Stage II P value<0.01).

Gut-Microbiota-Based T2D Classification

Figure 2:
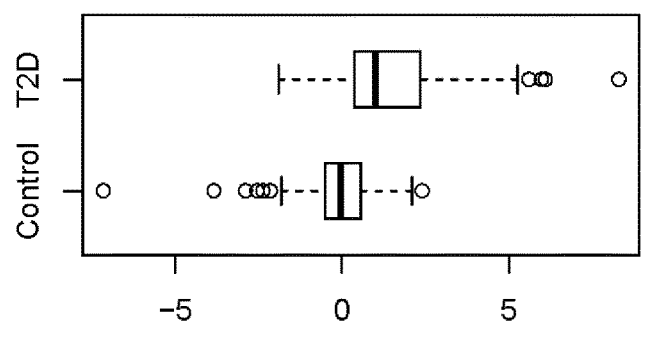
FIG. 2 shows a computed gut healthy index listed in table 3 which correlated well with the ratio of T2D patients in our population.

To exploit the potential ability of T2D classification by gut microbiota, the inventors developed a T2D classifier system based on the 50 gene markers that the inventors defined as an optimal gene set by a minimum redundancy-maximum relevance (mRMR) feature selection method. For intuitive evaluation of the risk of T2D disease based on these 50 gut microbial gene markers, the inventors computed a gut healthy index (Table 3 and FIG. 2) which correlated well with the ratio of T2D patients in our population (FIG. 1a), and the area under the receiver operating characteristic (ROC) curve was 0.81 (95% CI [0.76-0.85]) (FIG. 1b), indicating the gut-microbiota-based gut healthy index could be used to accurately classify T2D individuals. At the cutoff 0.046 where sum of Sensitivity and Sensitivity reached at its maximal, Sensitivity was 0.882, and Specificity was 0.58.

Example 2 Validate the 50 Biomarkers and Gut Healthy Index in Another 23 Chinese Individuals The inventors validated the discriminatory power of our T2D classifier using an independent study group, including 11 T2D patients and 12 non-diabetic controls (Table 4). In this assessment analysis, the top 8 samples with the highest gut healthy index were all T2D patients (FIG. 1c); the average gut healthy index between case and control was significantly different (P=0.004, Student's t test). At the cutoff 0.046, Sensitivity was 0.5833, and Specificity is 1. At the cutoff 0.290, Sensitivity was 0.833, and Specificity was 0.545. The results in Tables 3 and 4 below were obtained from the equation for the gut healthy index in section III supra. The resultant values presented in Tables 3 and 4 reflect multiplication by a factor of $10^6$ merely for ease of presentation.

TABLE 3

344 samples' gut healthy index

| 344 Samples' ID (Sign* represents T2D patients' samples) | gut healthy index |
|---|---|
| *T2D-056 | 8.277 |
| *T2D-049 | 6.082 |
| *T2D-092 | 5.968 |
| *T2D-070 | 5.596 |
| *T2D-036 | 5.265 |
| *DLF012 | 4.864 |
| *DLM023 | 4.596 |
| *T2D-051 | 4.433 |
| *T2D-050 | 4.220 |
| *T2D-072 | 4.051 |
| *T2D-083 | 3.689 |
| *T2D-015 | 3.633 |
| *T2D-096 | 3.485 |
| *T2D-060 | 3.449 |
| *T2D-019 | 3.354 |
| *DLM024 | 3.262 |
| *T2D-067 | 3.228 |
| *T2D-016 | 3.204 |
| *T2D-076 | 3.160 |
| *T2D-045 | 3.091 |
| *DOF002 | 3.075 |
| *T2D-087 | 3.069 |
| *DOM018 | 3.051 |
| *T2D-089 | 2.829 |
| *DOM025 | 2.752 |
| *DOM012 | 2.724 |
| *T2D-075 | 2.664 |
| *T2D-010 | 2.653 |
| *T2D-084 | 2.652 |
| *T2D-014 | 2.621 |
| *T2D-100 | 2.527 |
| *DOF012 | 2.523 |
| *T2D-020 | 2.523 |
| *T2D-103 | 2.518 |
| *DLM019 | 2.487 |
| *DOM013 | 2.431 |
| *DOM014 | 2.421 |
| *DLF001 | 2.420 |
| *DLM007 | 2.410 |
| *T2D-085 | 2.387 |
| CON-048 | 2.384 |
| *T2D-105 | 2.366 |
| *T2D-101 | 2.347 |
| *T2D-091 | 2.346 |
| *T2D-090 | 2.165 |
| *DOM008 | 2.140 |
| *DLM003 | 2.094 |
| CON-089 | 2.092 |
| CON-001 | 1.968 |
| CON-052 | 1.964 |
| *DLM022 | 1.959 |
| *T2D-046 | 1.934 |
| NLM017 | 1.916 |
| *DLM001 | 1.913 |
| *DLF002 | 1.857 |
| *T2D-081 | 1.816 |
| *T2D-059 | 1.779 |
| *DOM001 | 1.740 |
| *T2D-066 | 1.715 |
| *T2D-003 | 1.706 |
| *DOF009 | 1.692 |
| *DLM013 | 1.687 |
| *T2D-044 | 1.675 |
| *T2D-026 | 1.661 |
| *T2D-065 | 1.637 |
| *DOM022 | 1.628 |
| *T2D-077 | 1.628 |
| NOF009 | 1.594 |
| CON-092 | 1.590 |
| *T2D-102 | 1.575 |
| *T2D-008 | 1.570 |
| *DLM011 | 1.547 |
| *DOM005 | 1.502 |
| CON-041 | 1.476 |
| *DLM012 | 1.450 |

TABLE 3-continued 344 samples' gut healthy index

| 344 Samples' ID (Sign* represents T2D patients' samples) | gut healthy index |
|---|---|
| *DOF007 | 1.433 |
| CON-035 | 1.397 |
| *DOF003 | 1.389 |
| *DOF010 | 1.306 |
| *T2D-079 | 1.285 |
| NOF014 | 1.266 |
| *DOM016 | 1.261 |
| CON-083 | 1.242 |
| *T2D-054 | 1.240 |
| NOF006 | 1.212 |
| *T2D-055 | 1.203 |
| CON-080 | 1.188 |
| *T2D-041 | 1.168 |
| *DOM021 | 1.150 |
| NLM026 | 1.130 |
| *T2D-107 | 1.114 |
| CON-043 | 1.101 |
| NOM004 | 1.099 |
| *T2D-047 | 1.098 |
| CON-055 | 1.095 |
| NOM008 | 1.078 |
| *DLM027 | 1.065 |
| *DOF013 | 1.035 |
| *T2D-057 | 1.027 |
| *DOF014 | 1.026 |
| *DLF010 | 1.025 |
| *DOM010 | 1.020 |
| *T2D-068 | 1.019 |
| CON-050 | 1.018 |
| CON-032 | 0.996 |
| CON-067 | 0.975 |
| *T2D-080 | 0.972 |
| CON-004 | 0.971 |
| *DOF004 | 0.969 |
| *DLM014 | 0.965 |
| *T2D-030 | 0.954 |
| *DLF008 | 0.940 |
| NOF008 | 0.931 |
| NLM006 | 0.924 |
| NLM031 | 0.919 |
| *T2D-002 | 0.918 |
| *T2D-074 | 0.915 |
| CON-081 | 0.912 |
| *DLM005 | 0.900 |
| *T2D-001 | 0.872 |
| NLM023 | 0.870 |
| NLM007 | 0.859 |
| *DLM021 | 0.851 |
| *DLF009 | 0.849 |
| *DLF013 | 0.844 |
| *DOM019 | 0.832 |
| *T2D-031 | 0.828 |
| *T2D-024 | 0.824 |
| CON-073 | 0.787 |
| NLF014 | 0.764 |
| CON-085 | 0.761 |
| CON-006 | 0.750 |
| *DOM020 | 0.740 |
| CON-097 | 0.736 |
| *DLM028 | 0.715 |
| *DOM024 | 0.710 |
| *DOM026 | 0.709 |
| *DLM020 | 0.694 |
| *DOF006 | 0.690 |
| NOM028 | 0.683 |
| CON-086 | 0.682 |
| NLF012 | 0.674 |
| CON-039 | 0.665 |
| *T2D-093 | 0.664 |
| *DLM008 | 0.657 |
| *DLM015 | 0.648 |
| *T2D-078 | 0.646 |
| *DLM016 | 0.632 |
| *T2D-097 | 0.631 |
| CON-005 | 0.625 |
| *T2D-043 | 0.622 |
| NLM010 | 0.619 |
| CON-007 | 0.617 |
| *DLM004 | 0.617 |
| *T2D-099 | 0.614 |
| NOM023 | 0.606 |
| *T2D-013 | 0.597 |
| NOF001 | 0.595 |
| NOF011 | 0.582 |
| *T2D-018 | 0.573 |
| *T2D-029 | 0.569 |
| NLF005 | 0.565 |
| NOM007 | 0.557 |
| *T2D-082 | 0.553 |
| NOM014 | 0.548 |
| *DLF014 | 0.538 |
| CON-045 | 0.536 |
| NLF008 | 0.533 |
| NOF010 | 0.527 |
| *T2D-064 | 0.527 |
| NLM016 | 0.523 |
| *DOM017 | 0.522 |
| NOF012 | 0.522 |
| CON-068 | 0.511 |
| NLF009 | 0.479 |
| NLF007 | 0.477 |
| *DLF006 | 0.471 |
| NLM003 | 0.458 |
| *T2D-104 | 0.446 |
| *T2D-098 | 0.432 |
| CON-046 | 0.423 |
| NOF002 | 0.404 |
| CON-042 | 0.401 |
| *T2D-007 | 0.371 |
| *DLM009 | 0.369 |
| *T2D-006 | 0.369 |
| CON-079 | 0.353 |
| *DLF007 | 0.353 |
| NOM015 | 0.341 |
| *T2D-058 | 0.327 |
| *T2D-022 | 0.324 |
| *T2D-039 | 0.324 |
| CON-054 | 0.313 |
| *T2D-012 | 0.292 |
| *T2D-017 | 0.291 |
| CON-088 | 0.278 |
| *DOM023 | 0.276 |
| *T2D-021 | 0.262 |
| *T2D-063 | 0.258 |
| CON-018 | 0.253 |
| NLM024 | 0.253 |
| *DLF004 | 0.238 |
| *DOF011 | 0.237 |
| *T2D-028 | 0.232 |
| NLF010 | 0.219 |
| NLM029 | 0.202 |
| CON-021 | 0.191 |
| *T2D-025 | 0.182 |
| *T2D-052 | 0.177 |
| NOM005 | 0.167 |
| *DLM018 | 0.141 |
| *DLM017 | 0.134 |
| CON-082 | 0.133 |
| CON-099 | 0.133 |
| *DOM003 | 0.128 |
| CON-106 | 0.119 |
| NOM019 | 0.115 |
| *T2D-048 | 0.110 |
| *T2D-108 | 0.077 |
| *T2D-009 | 0.072 |
| *T2D-086 | 0.053 |
| *DOF008 | 0.048 |
| NOF013 | 0.047 |
| *DLF003 | 0.046 |
| CON-003 | 0.044 |

TABLE 3-continued 344 samples' gut healthy index

| 344 Samples' ID (Sign* represents T2D patients' samples) | gut healthy index |
| --- | --- |
| NLM015 | 0.044 |
| CON-053 | 0.043 |
| NOM013 | 0.038 |
| CON-047 | 0.035 |
| NOF004 | 0.034 |
| NOM001 | 0.030 |
| *T2D-023 | 0.027 |
| CON-044 | 0.019 |
| CON-013 | 0.014 |
| *T2D-005 | 0.010 |
| CON-058 | −0.001 |
| CON-056 | −0.004 |
| NLM002 | −0.010 |
| NOF007 | −0.016 |
| NOM010 | −0.027 |
| NOM020 | −0.031 |
| *DLF005 | −0.047 |
| NLM001 | −0.052 |
| NOM016 | −0.063 |
| CON-019 | −0.072 |
| CON-027 | −0.072 |
| CON-091 | −0.083 |
| CON-076 | −0.090 |
| CON-063 | −0.097 |
| NLM005 | −0.105 |
| *DLM010 | −0.107 |
| NLF015 | −0.109 |
| CON-096 | −0.117 |
| CON-098 | −0.126 |
| NLM027 | −0.129 |
| *DLM006 | −0.131 |
| CON-034 | −0.136 |
| NLM032 | −0.150 |
| *T2D-062 | −0.152 |
| CON-011 | −0.157 |
| CON-014 | −0.158 |
| *T2D-073 | −0.186 |
| NLF006 | −0.199 |
| NOM029 | −0.213 |
| NOM025 | −0.214 |
| CON-037 | −0.223 |
| NOM012 | −0.234 |
| CON-033 | −0.237 |
| CON-015 | −0.247 |
| *DOM015 | −0.253 |
| NOM026 | −0.264 |
| *T2D-011 | −0.278 |
| CON-064 | −0.279 |
| NOF005 | −0.286 |
| CON-002 | −0.288 |
| *T2D-069 | −0.291 |
| *T2D-053 | −0.292 |
| NLF002 | −0.312 |
| CON-087 | −0.313 |
| NOM017 | −0.329 |
| CON-061 | −0.337 |
| *T2D-071 | −0.339 |
| NLM004 | −0.360 |
| *T2D-106 | −0.361 |
| NLM025 | −0.364 |
| CON-060 | −0.380 |
| CON-107 | −0.405 |
| CON-084 | −0.408 |
| CON-090 | −0.411 |
| CON-093 | −0.419 |
| CON-062 | −0.427 |
| CON-022 | −0.455 |
| CON-028 | −0.487 |
| *T2D-042 | −0.489 |
| CON-070 | −0.495 |
| CON-078 | −0.502 |
| NLM021 | −0.520 |
| CON-066 | −0.576 |
| NLM028 | −0.605 |
| CON-040 | −0.623 |
| CON-020 | −0.626 |
| CON-075 | −0.626 |
| *T2D-088 | −0.628 |
| CON-059 | −0.646 |
| *DLM002 | −0.659 |
| CON-071 | −0.666 |
| NLF013 | −0.683 |
| CON-009 | −0.720 |
| NLM009 | −0.724 |
| NLF001 | −0.746 |
| CON-023 | −0.756 |
| NOM022 | −0.787 |
| CON-069 | −0.811 |
| NLF011 | −0.954 |
| CON-077 | −0.980 |
| CON-016 | −1.012 |
| NOM027 | −1.017 |
| CON-095 | −1.029 |
| CON-008 | −1.040 |
| CON-026 | −1.109 |
| NOM018 | −1.110 |
| CON-057 | −1.122 |
| *T2D-040 | −1.134 |
| CON-072 | −1.211 |
| NOM009 | −1.219 |
| CON-012 | −1.233 |
| CON-038 | −1.264 |
| CON-065 | −1.343 |
| CON-036 | −1.378 |
| CON-051 | −1.399 |
| CON-101 | −1.415 |
| CON-017 | −1.419 |
| NLM008 | −1.439 |
| CON-049 | −1.468 |
| *T2D-094 | −1.692 |
| NOM002 | −1.819 |
| *T2D-004 | −1.906 |
| CON-105 | −2.156 |
| CON-074 | −2.377 |
| CON-031 | −2.543 |
| CON-104 | −2.557 |
| CON-010 | −2.895 |
| NLM022 | −3.847 |
| CON-029 | −7.158 |

TABLE 4

23 samples' gut healthy index

| 23 Samples' ID (Sign* represents T2D patients' samples) | gut healthy index | Enrichment (1: T2D; 0: control) |
| --- | --- | --- |
| *HT14A | 6.749 | 1 |
| *ED11A | 6.585 | 1 |
| *HT25A | 3.521 | 1 |
| *ED10A | 2.609 | 1 |
| *HT8A | 2.248 | 1 |
| *T2D 189A | 1.124 | 1 |
| *T2D 198A | 1.122 | 1 |
| *T2D 206A | 0.936 | 1 |
| N075A | 0.600 | 0 |
| SZEY 101A | 0.531 | 0 |
| *T2D 207A | 0.493 | 1 |
| SZEY 103A | 0.467 | 0 |
| SZEY 93A | 0.413 | 0 |
| SZEY 106A | 0.347 | 0 |
| *ED16A | 0.314 | 1 |
| *T2D 192A | 0.290 | 1 |
| *T2D 195A | 0.231 | 1 |
| N104A | 0.138 | 0 |
| SZEY 95A | 0.124 | 0 |
| SZEY 90A | 0.085 | 0 |

TABLE 4-continued

23 samples' gut healthy index

| 23 Samples' ID (Sign* represents T2D patients' samples) | gut healthy index | Enrichment (1: T2D; 0: control) |
|---|---|---|
| SZEY 97A | −0.026 | 0 |
| SZEY 99A | −0.035 | 0 |
| SZEY 104A | −3.615 | 0 |

Thus the inventors have identified and validated 50 markers set by a minimum redundancy-maximum relevance (mRMR) feature selection method based on ~60,000 T2D-associated markers. And the inventors have built a gut healthy index to evaluate the risk of T2D disease based on these 50 gut microbial gene markers.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A method of determining Type 2 Diabetes in a subject comprising:
   (a) determining a relative abundance of one or more polynucleotides in a gut microbiota of the subject, wherein (i) the one or more polynucleotides are selected from polynucleotides comprising a sequence selected from SEQ ID NOs: 1 to 50;
   (b) determining a gut healthy index for the subject determined according to the relative abundance determined in (a), and
   (c) determining the presence of Type 2 diabetes in the subject according to the gut healthy index.

2. The method of claim 1, wherein step (a) comprises determining the relative abundance of each of the polynucleotides comprising a sequence of SEQ ID NOs: 1 to 50.

3. The method of claim 1 or 2, wherein the presence of Type 2 diabetes in the subject is determined by a gut healthy index greater than 0.046.

* * * * *

SEQUENCE LISTING

```
<160> NUMBER OF SEQ ID NOS: 50

<210> SEQ ID NO 1
<211> LENGTH: 393
<212> TYPE: DNA
<213> ORGANISM: Artificial
<220> FEATURE:
<223> OTHER INFORMATION: biomarker

<400> SEQUENCE: 1
atgaactacc tgatccgcga ccatgacgag gcactgttcc ggcatcgtca gcagatcatg      60
caggaggcag tcgatttcat caacaaaaaa tatggtgccg gcactgccga gatcaccatc     120
accgaaacct accggaacat gtatgagcag gtcaaaggcc acgagaagct tatctccaat     180
gtcatgactg ccatggagca ctgcggtatc accccgatcg tcaccccgat ccgcggcggc     240
acagatggcg cgcgtctttc ttatcaggga ctcccatgtc ccaacatctg taccggaggt     300
cagaatggcc atggacgcca tgaatttgta tccattcagt ccatggaagc tatcaccgaa     360
atgctgaagg agcttgtaaa actctttgcc tga                                  393

<210> SEQ ID NO 2
<211> LENGTH: 711
<212> TYPE: DNA
<213> ORGANISM: Artificial
<220> FEATURE:
<223> OTHER INFORMATION: biomarker

<400> SEQUENCE: 2
aaaaataaac ttcgacctca catgaatgac tactggtgta ttccgtcaaa agaagatgct      60
gattttgtag cctgcatgga agatgtcctt gatgtttatg aactcccata tgacccgatg     120
taccctgttg tctgtatgga tgaaaagcca taccagcttt tggatgatgt aaggcagcca     180
ctgcctgttc gtccgggtga caaccagaaa acggattccg aatataagag gaatggcacc     240
tgcagcatat ttgcttttgt tgaaccactt ggcggcagac accatgtgag tgtccatgaa     300
caccgtactg caattgactg ggcaatggaa atcaaatatc tgtcagatga aatgtttcca     360
gatgcaaaga aaatcatact ggtaatggac aatttaaaca cccataaagc tgcttcactt     420
tataaagcat ttccaccatc agaagcaaga aggatcataa aacgactgga aatccactat     480
acgcctaaac atggaagttg gcttgacatg gcagaaattg agcttaatgt aatgacacgc     540
caatgtcttt cgcgtcgaat atccaccctt gacaaactta aatgtgagtt atcagcatgg     600
gaaatggaac gtaatcggga tacagctaag atacagtggc atttccaaac agggggatgca    660 cgggaaaaac tgatatcact gtatccgaca ctatcatctg tcactttta a              711

<210> SEQ ID NO 3
<211> LENGTH: 933
<212> TYPE: DNA
```

<210> ORGANISM: Artificial
<220> FEATURE:
<223> OTHER INFORMATION: biomarker

<400> SEQUENCE: 3

```
atgccaggag taattgtagc actgattatt ttaattattg tagcactgct gatcgcagta      60
tcctgtgtta agatcgttcc acaggcgact gcatgcgtgg tagaacgtct gggaggttat     120
ctcgcaacat ggtctgtagg tattcatttc aaagcaccgt ttatcgaccg tgtggcaaag     180
agagttgtat taaaagagca ggtggtggat ttcccgccac agccggtgat cacaatagat     240
aacgtaacaa tgcagatcga taccgttgta tatttccaga tcacagatcc gaaactttat     300
gcatatggcg tggagaaccc gatcatggcg atcgagaacc tgactgcaac cacactgcgt     360
aacatcatcg gtgatcttga actcgatgag acactgacat ccagagagac gatcaatacc     420
aagatgagat cttcttttgga cgttgcaacc gatccttggg gaatcaaagt caaccgtgtt     480
gagttaaaga acatcatccc gcctgcagca atccaggatg cgatggagaa acagatgaag     540
acagagcgtg agcgccgtga agcaattctt cgtgcgaag gtgagaaaaa gtcaaccgtc     600
cttgttgcag aaggaaagaa agaatcagca attcttgatg cggaggctga aaaacaggca     660
gcgatcttac gcgcagaggc aaagaaagag caacgatcc gcgaggcaga aggtcaggca     720
gaagctattt taaagatcca gcaggcaaat gcagacggac ttcgcatgat caaagaagct     780
gcaccggatc agaatgtgat ccagttaaag agcttagagg catttgcaaa agcagcagat     840
ggaaaagcaa ccaagatcat tattccatct gagatccagg gaatcgcagg tcttgcaaaa     900
tccgttacgg aaattgcagt agatcataaa taa                                  933
```

<210> SEQ ID NO 4
<211> LENGTH: 336
<212> TYPE: DNA
<213> ORGANISM: Artificial
<220> FEATURE:
<223> OTHER INFORMATION: biomarker

<400> SEQUENCE: 4

```
atgtctgacg tcgtagcggg tatcatcgta gccaccatcg cccttccgtt atctatcgcg      60
ctggcactgg catccggcgt gggtccggag cagggtatct acacggcgat cgcagcagga     120
tttgtgatct cattcttagg cggcagccag ggacagatcg cggaccgac agcggcgttc     180
gcgacgatcg tagccggcat cgttgcgaga agcggcgtgg aaggtctggc agtcgctacg     240
atcctggcag gtatcatcct tgttatcatg ggattctgcc agcttggttc cttaattaag     300
tttatcccgt ttacgattac caccggattt acctcc                               336
```

<210> SEQ ID NO 5
<211> LENGTH: 354
<212> TYPE: DNA
<213> ORGANISM: Artificial
<220> FEATURE:
<223> OTHER INFORMATION: biomarker

<400> SEQUENCE: 5

```
gaggcatcga agatcacctt cacagcagag catctggcat ctcttatcgc actccttgag      60
aagagcgtta tcaacaacca gactgcaaag gatgtgtttg ccgtcatgtt tgagtctgat     120
gtggatccgg cagcttatgt tgaggaacat ggactcagga tggagagtga ttccggactt     180
ctggaggaaa cagtgaagaa gatcttggac gcaaacccga aagctgtggg cgagttaaag     240
gaaggaaaag acaaagtcat cggattcctt atgggccagg tcatgaagga gatgaaagga     300
```

| | |
|---|---|
| aaagcaaacc cgtcacaggt gagcgggatg atccataaac ttgtgcagga ataa | 354 |

<210> SEQ ID NO 6
<211> LENGTH: 1038
<212> TYPE: DNA
<213> ORGANISM: Artificial
<220> FEATURE:
<223> OTHER INFORMATION: biomarker

<400> SEQUENCE: 6

| | |
|---|---|
| atgtcatgta aaggagggac tttattggaa gtagtaaatt caatatggct attttttcaa | 60 |
| gaccaaatat taggtatgaa atggttgaat ggcttaattg gtaatgggct atcattgcta | 120 |
| gggctagaca ttaacagtcg tttaggtgga agtattcaat tcttttata cgatgtaatc | 180 |
| aaaatcacaa tcttgttatg tttactgatt ttctttatat cgtatattca aagttatttt | 240 |
| ccacccgaac gaagcaaaaa aattttaggg cgatttcatg gtatcggtgc aaatatcata | 300 |
| tccgcattgt taggaacagt tacaccattt tgctcatgtt cttctatccc gttgtttata | 360 |
| ggttttacaa gtgcaggatt accgttagga gtaacttttt cctttttgat ttcttcgcct | 420 |
| atggttgatt taggaagtct tgtattgcta atgagtattt tcggggctaa agttgctttt | 480 |
| gcttatgtga ttgtaggctt gataatcgct gtaattggcg gtactttaat tgaaaaaatg | 540 |
| cacatggaaa aatatgtgga agatttcgtg aaaaatgcaa gtaatgtcga tattagttct | 600 |
| cctactttaa ccaaaaagga tagagttcaa tatgcaaaag aacaagttgt aggaacattc | 660 |
| aagaaagtat ttccatacat tttgattggt gtgggtatcg gagcagttat ccataactgg | 720 |
| atacctgaaa catggattga agtatcttg ggcagtaata acccgtttgg tgttatttta | 780 |
| gccactcttg tcggagttcc tatgtatgct gatatttttg gaacaattcc agtagcagaa | 840 |
| gcattacttt caagggtgc acaattaggt acaatttat catttatgat ggctgtaaca | 900 |
| acattgagtt tgccgtcttt aataatgctg aaaaaggcag taaagcctaa actattgacc | 960 |
| cttttattg ccatttgtac gtttggcatt attattgtag gttatctctt taatattttt | 1020 |
| agtacattat ttatttaa | 1038 |

<210> SEQ ID NO 7
<211> LENGTH: 948
<212> TYPE: DNA
<213> ORGANISM: Artificial
<220> FEATURE:
<223> OTHER INFORMATION: biomarker

<400> SEQUENCE: 7

| | |
|---|---|
| ctttgcggcg cttacgctga tgctggctgg ctggcatttc attccgcagc atttaaatac | 60 |
| agcatttatc ccgctggtaa tgagcatttg gctccgttcg ggatatggcg tttacagaaa | 120 |
| aatatggaac atcgggtacg gaaaatatta acatcgctta tcgcaattct ggcagcaacc | 180 |
| aatctggagg ctcaacaaag cacgcccaaa ttggtcgtgt gcatcaccgt cgaccagttg | 240 |
| cggggcgatt atatagaata cttttataat acattcggcg aacgcggttt caagcggttg | 300 |
| atgaatgaag gactggtgta taacaacatc cggttcgaat tctctgacat cgacgaagcc | 360 |
| agtgcctttg ccaccctatt taccggaagt aatcctaatt tcaacggaat atcaggaaag | 420 |
| aatatctacg attttgacaa ggaaaaagag gtttcggtct tatatgatcc ggactatatc | 480 |
| ggcaattata cgaaagaaca ttattctccc cggaaactga tcagctccac gatcggagat | 540 |
| gaactgaaaa tagcttccaa aggcagaagt gacgtatatg ccattgctcc taaccccgaa | 600 |

| | |
|---|---|
| agtgcgatcc tttctgccgg acatgcggca aacggtgctt tttggatgga cgattacaac | 660 |
| ggcaaatggg cgacatcgac ctactacaaa gggcttcctt ggtatgtgga ccgctacaac | 720 |
| aacggcccgg aatccctgtc ggcccgtttg gagcagatgg cttggacacc gtctttgtca | 780 |
| ccggacaagt tcaacgcatt cccatacgta ttagacgaga tacctttcaa atatacattc | 840 |
| aaagaaaata cgaacgagtg tttcttcaac ctgaagacct ctcctttat caataaggaa | 900 |
| atcaatcgct tggcgcttca gttcctcgaa tacggggctt tcggtaca | 948 |

<210> SEQ ID NO 8
<211> LENGTH: 486
<212> TYPE: DNA
<213> ORGANISM: Artificial
<220> FEATURE:
<223> OTHER INFORMATION: biomarker

<400> SEQUENCE: 8

| | |
|---|---|
| attcaacaat ccattccaat ggcggcctcc gtagctaccg aggatacgct gaagtttacg | 60 |
| gattttcatt ctatgggagc aacttacgct gtacatttga agctgtgaa ccgaaagaac | 120 |
| cggcagacga aggaaggctg ggtgagttgt ggcagctata tctttccata catatcgctc | 180 |
| caactggatg atgcggtcag tatggtgatg ccggaacggg aaccgagacg ctttgcctcg | 240 |
| gacgtaatgg tctatacgaa aaataaacag accaaggagg cgtgtatcga ggtgaataag | 300 |
| ccactctcta ttgccggatg gaaaatctac caattgagtt acgacgagac gaaaggtaaa | 360 |
| tggagccgga tgagtgtatt tgagttggtg agagatccat ggttgccgat cgtttataca | 420 |
| gggatcttaa tgatgatagc cggggcgatc ggattattcc tatccgctcc tgtaaaaaaa | 480 |
| gaatag | 486 |

<210> SEQ ID NO 9
<211> LENGTH: 4005
<212> TYPE: DNA
<213> ORGANISM: Artificial
<220> FEATURE:
<223> OTHER INFORMATION: biomarker

<400> SEQUENCE: 9

| | |
|---|---|
| aaaaaagcaa aaataaaaaa agttgatatc ttgcaaacga acatggaaa acatcaacag | 60 |
| ctcatgaagt ttcaaattgt gctattatgc ttattcttct tagtagaact gaatgcaacc | 120 |
| ccattctact ttaagtccta tgacatggaa gacggattaa gtaataatca tgtcacatgt | 180 |
| tgcgtacaag acgactatgg ctttatgtgg tttggtacca gagatgggct caatagattt | 240 |
| gacagcaaaa aattctatac attcaagagc tactcttcag aaaaaggctc tttaatgagc | 300 |
| agttatattc ttgacttagc gaaaagtccc accggacaaa tttgggtaag taccaacctt | 360 |
| gggctacaaa aatatgacta tcaaacagat tccttcacac tcattgattt caccaaagga | 420 |
| atcaactgtt attcactaca atttgaccag caaggaaatc tctggatgat tcttaatggg | 480 |
| tactcactcg taaaatacaa tgaaagtcaa ggtatgcatc ttaattatat gtataaagga | 540 |
| agtgatccta ttacctcctt ttatataact cctcaagacc aaatttgggc aacaacagcg | 600 |
| aatggtaatg tcgttttct agatgatgac aaaaatgaat tcatagcctt agatatcaag | 660 |
| aatctagata aaaatcatcc tatcgatgat atgacagcaa tatgggcctc tccttagat | 720 |
| aatatattat taattggaac taagataat ggtataaaac gaatcgatat acagacaaaa | 780 |
| acatataaag atattttacc tcaacaaaaa aaatctccac tttatactag aaatatcatt | 840 |
| cgtatgacaa aggagaaagt atggattggc acttttaatg gcatatattt atatgatatt | 900 |

```
caaaatgata cgataatgtc tatccagcaa aataaaagtg acctctattc attatccagc    960
aatgctatca aagaactcta caaagatcaa gaaggaggta tctgggtttg tactgataat   1020
ggcggtatca gctactctcc tccttattca aaattcaaaa ggcactataa tattcctgga   1080
caaagaacgc tcaatggaga tattatacac gatatttgca tagacaaaaa taataatcta   1140
tggattggca cagaagacgc tggattgaat aagctaaaca tgaaggacca ttcatataca   1200 tctttttaatg acatgaaagg cctttcacaa aattgtatac atggattagc gtctatagat   1260
aatcacctat ggatagggac acacgctaat ggtattgatt taatggatat ccgtactgag   1320
aaaataatca acattacac gatttccgta atccttatg caaacaaaaa cgacatcatc    1380
gtataccttt ataaactcca aaacaatgat tgctggtag ctaccgctct tggtgtctat    1440
caatataatt ctcaaaaaga catttttgag aaattaagcc aatttcctaa taattgtagg   1500
atacaaactc tttttgaaga tcatgatgga gtaatatggg ctggaacatc gagtaaagga   1560
ctatattatt ataatcctgc tacttcccaa cacggagaat ttaaattaga tacagtaaat   1620
acaagccgaa caataaacaa tatttatgaa gatcgtaaga caacttatg gttcgcaact    1680 ggtgacggaa tcaaaattta tgaccgtagt actcaacaaa cgaccaaata cgatatgcaa   1740
gatggcttac ctagcaatgt aatttaccgt attgaagaag ataaaaaagg aaacatgtgg   1800
atcagtacgg ctaacggcct cgcaagactc aaccctaaaa accataaaat aaagtcttc    1860 aaaaaagaac atggattaac ttcaaatcaa ttcaattata actcttcttt aaaaacagat   1920
aatgacaaat tatattttgg gacactaaag gggatgatta gcttccaacc taatagtatc   1980
caagaatttt ccattcaacc gaaagtatat atatcacaga ttaattataa tgatccagat   2040
cataacttct tacaccaaga ggctatcact tttaaaaaag gaatcacctt agaacataat   2100
cagtccacat tctacatcga ctacacatca ttaagctacc aagctcccaa cctcacccaa   2160
tacgcctatt gcatggaagg gttaagttcc aaatggtatc atgtggtggg cgagaaccgg   2220
gtttatttca caaaactacc gcccggtaat tatacgttca aggtgaaggc ggcgaacctg   2280
tccggtattt ggaatgatga gccggcgatg ttccagatta cgatccttcc cccatggtgg   2340
ctctctacca aggcgttaat cctatatggg attatcgcta tcggatgcgt agtgttgctg   2400
atctttatca tttcccggca taataaggcc aatatacagc agaaaataca ggagttcgag   2460
aatgaaaagg agaaggagct ttatcaagct aagattgatt tcttcatcaa tatcgctcat   2520
gagatacgta cgcccctaac tttaattaaa agtcctctgg agaaagtaac acgggacatc   2580
aagctatctc ccagcgcaaa gaattatctg acgattgtgg ataaaaacgc gaaccggcta   2640
ctggatctgg tgaatcaact actggatttc aggaagacgg aaatcgaggg atataaacta   2700
aacttcatac atacggacat catcgcattg atgcaagaga cctttgagtg tttccacgat   2760
acggcggagc aggaggcatt gcaaatgatt atcgagtgta acgtgaaatc tttctacgcc   2820
tttatcgata aggaggcttg cacgaagata ctccagcaacc tcctatcgaa cgctattaaa   2880
tacgcaagaa gcaagatcat cgtccggttc gagacgcaag atggcgagcg attcacgatc   2940
gatatcatga cgatggaaa gcccatctcg gaggagataa aagaaaagat cttcgagcct   3000
ttctaccggg atgactcctc tatccataaa tccgggaccg ggctcggact acccttggcc   3060
cgttctttag cggagatgca cgagggatcg ttgacgttgg aggaatctcc gactgggctt   3120
atcatcttta gattacgttt gccggtgaac caaccgaact cattaaaact agaggaagag   3180
aaagcagagg tcctgaccaa ccctgccagc gagcggaaat atgtcaccca agaatcccgc   3240
```

| | |
|---|---|
| ccgacggttc tcgtggtgga agataacacc gaaatgctcc atttcatcgg tcaagagatc | 3300 |
| aatgtccatt acaatgttgt caccgccggt aatggcgagg aggcgattgc ccgtcttcag | 3360 |
| gaatatggca tccaattaat catcagcgat atcatgatgc ctgtcatgga tggtttcacc | 3420 |
| ttattgaaaa agataaagac taatctggag ttcagccata tcccgatcat cctcctgacg | 3480 |
| gctaagaaca ccttgcaatc tcgcatggaa gggcttgagc tgggggcgga cgcttacatc | 3540 |
| gacaaacctt tctccatgga tctattgctt acccaagtga cgaacctgct gaacaaccgg | 3600 |
| agcaatatgc gtgcctatta tttcaactcg ccgattgcca atatcaaatc catggcttac | 3660 |
| acgaaggcgg acgagaagtt cttgaagaaa ctgaacgata tcatcgacag ccatataaac | 3720 |
| gacgtgaacc tagacgtgga catgatagcg gacttgatga atctaagccg tccgacccct | 3780 |
| taccgtaaaa tcaacggcct gtcgaacgta acgcccaacg agttgatcaa gatcagccgg | 3840 |
| ctaaagaaag ccgccgagtt gatccttcaa ggcgatatga ggatttacga gatcgccgag | 3900 |
| gcggttggtt tcaactcgca atcctatttc agccgggcct tctccaagca attcaacatg | 3960 |
| agcccctcgc aatacgcgaa agaaaataat atcgaattga aatag | 4005 |

<210> SEQ ID NO 10
<211> LENGTH: 1314
<212> TYPE: DNA
<213> ORGANISM: Artificial
<220> FEATURE:
<223> OTHER INFORMATION: biomarker

<400> SEQUENCE: 10

| | |
|---|---|
| atggatatga taatcattct cgtaggactt gcattgttac tagtccttac attaaagaaa | 60 |
| gtgccggttg tatatgcagc ggcaatcagt gttatatttta tagcactttt cagcagactt | 120 |
| ccagttgtat caactatgac aggtgattat atgactggat ttgcaaactt tgttaaatca | 180 |
| tcatggctta tgctgttgtt aggtgccatt cttttcaaagg tcatggatat tacaggagca | 240 |
| gcaaggtcaa tagcttcatt tattattggt aagcttggtg ttaagtttgc tataccagct | 300 |
| atcgtaattg ctggtggact tttaacttat ggtggcgtat ctgccatggt ttcatgtttt | 360 |
| gcactttatc caatcacact tgcggtattc agggaagctg atatgccaag aaagcttata | 420 |
| cctgcaacaa tcggtgctgg tatattcaca tgggtaacaa tgttacctgg taatcctcag | 480 |
| gtgcagaata ttattccatc atcatttctt ccaactaatg ctatggcagc tccagtagtt | 540 |
| ggtgttgtat gtggcgtttt tacacttgca cttattctgg tttatcttat gtgggagtca | 600 |
| aacagagcaa ggaaaaatgg agaaggcttt attgttgatg aagaaacatc caaagtcctt | 660 |
| gcaaagacag atgagatgga agcaaatgga aagctgccta atgtagtact tgctattctt | 720 |
| cctatcgtat gtgtagcagt tgtactgaat gtattaaaac aggatatatc agttgcactt | 780 |
| ttatcaggaa ttgttctttg ctgtatatta ttctttaaga atattacagg agtacagaag | 840 |
| ctgcttacag atgcagtcag cagtgcagca gttacaacta tcaatgcatc agctatagta | 900 |
| gccataggtt cagtagttaa agcagcacca ggatttaacc agattgttaa tggaattctt | 960 |
| aactttagta catcaggtgg taatccactt attatatttg gtattgctac tacattatta | 1020 |
| tgtggactta atgcatcagg tatgggagga ctttcaacaa cactttcagt acttgcagaa | 1080 |
| ccatttatgg ctatgggagt taatccagct ataatgcaca gaataggtgt tattgcatct | 1140 |
| gtaggtcttg acagtcttcc tcatagcggc ggtatcgttg cagtccttgc tatatcggga | 1200 |
| gtttcataca aggaaggtta taaatatttta ttccgtagtaa cagttgttat tacattactt | 1260 |
| gcactcgcac ttgccttagt acttggtaac attatgtatc ctatagcagc ttaa | 1314 |

<210> SEQ ID NO 11
<211> LENGTH: 2427
<212> TYPE: DNA
<213> ORGANISM: Artificial
<220> FEATURE:
<223> OTHER INFORMATION: biomarker

<400> SEQUENCE: 11

| | | | | | |
|---|---|---|---|---|---|
| atgaaaaaat | caagaagaag | tcagcttctg | cagcatattg | cagaaatcac | atccatcgct | 60 |
| attgcgaata | agaatatac | tggtatcaat | accgacgcct | ttaccatcag | tctcgatctg | 120 |
| aatcttgacc | gtgctaatgt | cagtcgtatg | ctgaatgatc | tgtggcggga | aaatattctt | 180 |
| atcaaaatac | agggacgccc | cacctttat | ctgcaccgta | aaacactgct | gaagcgctat | 240 |
| cccaattcct | atataccagc | gctcatacct | aaaaatgaag | agcttgccac | ttatctggag | 300 |
| cactcgcttg | tactctctca | ggaaacagcg | aaggaagcat | ttaccagttg | cattgggcat | 360 |
| tccattcggg | agagtatgta | tcccatcatt | gaggacatca | aggtctttct | cacctatcca | 420 |
| cagaccatgc | gctccatcat | gatctgcggt | ccgcacaaaa | gcggaaagca | tcatctatta | 480 |
| cgctgtatca | tacaatatct | gaaaattgac | acagaacagc | tacttcatat | tgactgcgca | 540 |
| gcaatcgcgt | taggaaagct | gacaatttct | gacattatgc | agcgaatcga | tacaagcctt | 600 |
| gatcaggaaa | aaagcaacat | catcctgttt | gaaaacctgg | atgcactcac | ggaactccct | 660 |
| gcaagcatta | cgacgatgga | aaccttgctc | cgcttttatc | agcgaatggc | agagagcaat | 720 |
| gagctgaacc | tgctatttct | tgccgtgact | gcaatgaatg | aacactttct | acagctgcaa | 780 |
| aagctgtttc | agaaggtata | tgagctccct | gatttgaata | gcagaacatt | aaaggaaaag | 840 |
| tatgagtttg | tgttgcattt | tatgcaaaat | gaagcagatg | caatcggtaa | gacgatttct | 900 |
| ctatcctcct | ccattctaaa | ttgctttgcg | actgcatgct | atccggggaa | tctacagtat | 960 |
| ctgaagcagg | aactgcgaca | cgcccttttcc | tatgcataca | tacaatcctc | acaacagcag | 1020 |
| gaaacctta | tcactattga | ttatcagcat | ctctcagatg | aactgcttgc | cagtatccgc | 1080 |
| aatgtatccg | atatacttcc | catcatagaa | agcattacct | ccacactgca | ggaaaaaaat | 1140 |
| cactttctga | ttccggagac | agaatgtatt | ccctgcaaa | agctgctgca | cagctgtatt | 1200 |
| caggaggatg | gtatcctgca | ggcattcaca | caccgggagc | caagactgtc | cgaatactgt | 1260 |
| aagcaggagc | tgcgcaatgc | cgcaaagctg | gaaatcaatc | agctgtattc | actgtcatta | 1320 |
| cagaagatac | gggactgcat | acagcaggtt | ttggataaac | atgccttcac | aatacaggaa | 1380 |
| aagcagctgg | ataagctgtg | catacgtata | acaatctat | tttccatatt | gaagcatcac | 1440 |
| tcctattcca | ccgcgttcgt | ccccgatatg | gatatgcagg | atactgctat | acaattgctt | 1500 |
| tgtgaggaaa | tatgtgaagc | attaaaacaa | acctttgata | gaaagcttcc | ggatatggag | 1560 |
| cagttgttca | tgtattgtta | tctgttgtat | tccagagagc | atcacataaa | gggcagcatc | 1620 |
| gctgttttgg | ttgcctgtca | gggtgaggga | attgctgaaa | aatatgccac | ccatgtaaat | 1680 |
| actatgaagt | atcaggtgaa | atgccggtac | attgatgaaa | ctggtacagc | atccacaaga | 1740 |
| aatctgacag | cctttctcag | taccgttgtg | gataaggtaa | gggaaattga | tgagggaagc | 1800 |
| ggtgttgtca | tcattaccga | ttttaatcct | ctgcttgatt | ttgattccga | aattcgcagc | 1860 |
| agtacagata | tcgaaacggt | aacgctttcc | ccaacctcac | tgccgcttct | gattcaggtg | 1920 |
| atgaatatgg | tgaacaatcc | atctatacag | ctggaggata | tacggaatta | tgactatgga | 1980 |
| accgccctgc | agataccgca | gagcgattcg | acaggctatg | gtattgagat | acagaaaacg | 2040 |

```
ctggatgatg tagcggacaa aattctatca gaatctcttg tattcctgaa tccgaagaaa    2100
gctacaatgg cattgtttcg agtattgatg aaaatttatg aggatctcgg actaaattat    2160
actgatgaaa tatccatccg ttttattttc cacagtgcgt ttatgattga gcgtgtaatt    2220
cgtagagaac cgttgatcta taaaaataca aacagtatca tttccacaag ccgtgaggtt    2280
tatacttcca ttgaccgcaa catggagctg gtgaatgatg tattcggtat cagcattcca    2340
tccagtgaaa ttgcacgact ttctgaaatt tttgttgatc ttatcaatgg ttgtgaacag    2400
gaggaatgta ggacaggcat tgattga                                        2427

<210> SEQ ID NO 12
<211> LENGTH: 201
<212> TYPE: DNA
<213> ORGANISM: Artificial
<220> FEATURE:
<223> OTHER INFORMATION: biomarker

<400> SEQUENCE: 12
atgatccttt cggcggtttg tattgcgctg gggctgctgt gcctgcttcg tccggcgctg      60
gtttggaaat ggaccgagca gtggaaatcg taccgcgccg atgagccgtc ggagttatac     120
aggttcggca tccgtttcgg gggcgcactg ttcctcgttt cggcgttgt ccttccgttt      180 ctgccgctgc ttttgaaatg a                                              201

<210> SEQ ID NO 13
<211> LENGTH: 999
<212> TYPE: DNA
<213> ORGANISM: Artificial
<220> FEATURE:
<223> OTHER INFORMATION: biomarker

<400> SEQUENCE: 13
atgaagatat tccttccggt gatgtttctt ctgatcgcgt tcccggttgc ggcgtggttc      60
gtgttcagct atgcgctgga cggacatatg aactacaacg cgaagcgtga cctggggcag     120
atggtgaaga ccgtggagga actggcggac gaatacagca acctggacgt gccggacgaa     180
actaatgcgc cggatgccgg gaagagtctc ttgagtgccc tgcggaacgc ggctcagaca     240
gagtccgggg agtcgaaaat gctggtcatt ggaaataatt accgggtgct gtacccgaaa     300
aactatgatg accagccgga gatgacccag atgtactcgg aatttctgac agaaatgacc     360
ggaaatgatc cggcgttcga gagcggggag atcacggagg agaccatcgg tgacacaaaa     420
tatatgctct attttctgga tgtgggtcag aaccggcccg tcatgtcca gaatgtgctc      480 ttatactgtc cgatccacga taccagcgtg atcttaaatg aggtgtcgag actggtgctc     540
atgattatgg gagcgatggc gggcgtgtcc attgtgctgt tctggttcgt tgcgggaagt     600
atttcgactc cggtgagccg tctctgcgaa gcagcccggg gaatcggtga agaagtttt      660 aagaaagtcg agactgggac caacgtaaag gagctctacg agctggagaa cgagatcaac     720
cagatgcagg acaatctctt aaaggcagac gaggcggagc gtgtgttttt ccagaacgcg     780
tcccatgagc tcagaacgcc gcttatgtcc atcagcggtt atgcccaggg aatccagaga     840
ggcgtctttg aggatgtctc ccaggcagca ggcgtgatcc tggacgagag cagccgcctg     900
acggaagttg ttgacgggat cctgacgttg acgagaatgg accagatgcg gtaccaggtc     960
gtgccggtgg agttggggat ccgggagtac atcgaggac                           999

<210> SEQ ID NO 14
<211> LENGTH: 804
```

```
<212> TYPE: DNA
<213> ORGANISM: Artificial
<220> FEATURE:
<223> OTHER INFORMATION: biomarker

<400> SEQUENCE: 14
ttggcgctca aggagctgga aaatgagatc gggacagagc ttttttaagag aagcaaccgc    60
ggcgttgtcc tgacaccgga aggacaggag ttcttaggct acgcgagaca ggtaacggaa   120
cagtgtaagc tgatggaatc cagatatatt gagaaaaaga acgtgaagaa gaaattcggc   180
gtttccatgc agcattacac attcgcggta aacgcgttta tcgagatggt aaagcagttc   240
ggtatggatg agtacgagtt cgcggtccgg gaggagaaga cctatgaggt cattgaggat   300
gtgaagacgt tcaggagtga gatcgggatc ctgtatctga acgatttcaa ccggaaagtg   360
ctcacaaagc ttttcgatga gtccgacctg gaattctgcc cgcttatgga ctgcgggatc   420
tatgtatatc tctggaaagg ccatccgtta gcgaaccaga aggagatcac catcgaggag   480
cttcaggagt atccgtgtct ttcctttgaa caggaaatt acaactcctt ctattttgcg   540
gaggaggtgc tgagcactta cagctataaa cagctgatca aggccaatga ccgggcgacc   600
ttgttaaatc tgatggtagg ccttaacgga tatacctct gttctggaat cctttgtgat   660
aatttaaacg gttccgatta ctgggcggtg aaattaaagt ccgacgaggt catgaccatc   720
ggatacttaa agagaaaagg gatcggcctg agcccgctgg acagaagta tctggaggag   780
atccggaaat tgaaggcat gtag                                           804

<210> SEQ ID NO 15
<211> LENGTH: 972
<212> TYPE: DNA
<213> ORGANISM: Artificial
<220> FEATURE:
<223> OTHER INFORMATION: biomarker

<400> SEQUENCE: 15
gtgcggctag aaaaaacgac ggaggttgag atgatgcaat caatatcaag ttatattaat    60
cctaatacaa gaggacttac atctaattac aaaaatacag ctattaaaga taaggaagcc   120
tataatgagg cgatgtcgca gcacttacta aatccggtag aagatttggt tcaagtgtta   180
aaaacaccta taaaattggc gaggagttca tcacttagca gacagaataa ttctgttaat   240
attgcagaag ggcaaagaat ccgtgttaat ggaggtcatg tgcttacggt tacggcgcat   300
ggagtagaag tttctggtgg agataaccca tatgatacag aatcctatgt aaaagcacaa   360
agaatggcag atgcgttggc atccatgctg cgaaatgcag tgggacaat gactactgta   420
gcacattcaa aggaggaata tgccaggtat acagaaggaa ttacggatgt gatgtcttat   480
ctggggatag acacttccaa agatttcacg gtcaatggta tgcgatatag caaaaataaa   540
gatggttggt atgagtcaga agcgaacagt gatgcgcagg cggcatatga acagttaaaa   600
gcgaataaca gaacctatca gtttgcagat gaaaagacca aaaagcagat tacatatatt   660
agtgattatt accttcaaac agtgccggag agtgtcaagg cggcgtggca ggaaacattg   720
gttgaaactg gttttaatcc atttcagacg gatgtaacca gtacattaac gcagttatct   780
gtggagcagg attttctgac aggtggtgat gacaatattt ttggtgaaac gaaagaaagt   840
tgtttagcag ctatcgacaa agtattggag agaatagaaa atccgttggc agcagttaca   900
gaggaaagag cagcatatct gcagcaggaa aagaattttt atacagtgct cgcatctaag   960
atacgagaat aa                                                       972
```

<210> SEQ ID NO 16
<211> LENGTH: 1107
<212> TYPE: DNA
<213> ORGANISM: Artificial
<220> FEATURE:
<223> OTHER INFORMATION: biomarker

<400> SEQUENCE: 16

```
attggcgatt tctgcaagaa ggaaattgag cccatcatgc tggattggga caaggttgtt      60
gacccttcca aggcaatccc ctttgagccc tatgcaaagg cgttcaagct gggcctgaac     120
tccttcgaga ttcccaagga gtacggcggc aacaaggtcg acctggctac cgctgaggtt     180
atgtacgaag agatgggcta ctatgacggc aacttcgctt ccgtcatgca gaccaccaac     240
ctggctctga gcccattct gatcggcggc accccgagc aggttcagta cttctccaag       300
cacatcctgg agggcaaggg ctacgctgcg ttcgctctga ccgagcccca gtccggttcc     360
gacgcttcca acgtgaagac cactgctgac aaggacggcg acgagtgggt catcaacggt     420
gagaagtgct tcatcaccaa cggcggcgag gccgacatcg tctgcgtgtt cgcttctacc     480
gatcccaccg ctggcaccaa gggcatctct gctttcatgg ttcccaccag cacccccggc     540
ttctctgtca ccaagtatga ggacaagagc ggcttccgta ccatctccac ctgctccctg     600
aagttcgaca acgtccgtgt tcccgctgcc aacctggttg gtggtgaggc tggcctgggc     660
aagggcttcg gcttcgctat gaagaccctg acaagtccc gtgcttgtgt gggtgctctg     720
gctgttggta tcgctcgccg cgctctggac gaggccatag cttcgtcaa ggagagagtc      780
accttcggtg ctcctgtttc caagcgtcag ggcattcagt ggatgatcgc tgacatggcc     840
accaagattg aggcttcccg tcagctggtc tcccacgcca acgacctgca gagcaagggc     900
ctgcccttct ccaaggaagc tgctatggct aagatgttcg ctacccagtc cgctatggaa     960
gtctgcaccg acgccatcca gctgatgggc ggcaagggct acatgaagga agactgcgtg    1020
gagaagctgt ccgcgacat caaggcttac tgcatcttcg agggcaccaa ccagatccag    1080
aagatcgtta tctctggcgc tgttctg                                        1107
```

<210> SEQ ID NO 17
<211> LENGTH: 537
<212> TYPE: DNA
<213> ORGANISM: Artificial
<220> FEATURE:
<223> OTHER INFORMATION: biomarker

<400> SEQUENCE: 17

```
atgtctaact ttgtgcaaaa ggagaaagga gcacacaata tgccgttttc gtttaatttc      60
ggcggcttta atccgggcga tttcagcggg tttggaggat ttcaggacga ggggccgca     120
ccccgccaa aaagccccg caaacccgc aaggccatcg gcaacgcctt caccaggacc       180
ctgatcaacc tgggagtaac cctgttttc gctctggtct attttatgt ggaactgccg       240
gcgctgaact tccatgcgga ggagttctac gtattcgcat ttttaatctg cgcggtatac    300
tgcatctgcg cggttgtgac ctccggcttt caggggagg gaatcaaggg ctatgtcggc     360
tttgtgaaaa aacagtgcgt cattccttc ctggccttca ttgccctgat cgccgctatt    420
gccattggag cggtcacatc ctgggtggtg ctgcgggcgg gcagctacag cgagctgctg    480
agcattgaga ccggggactt cgcctccgag gtggatgaga tcagctacga tcagatt       537
```

<210> SEQ ID NO 18
<211> LENGTH: 474

<212> TYPE: DNA
<213> ORGANISM: Artificial
<220> FEATURE:
<223> OTHER INFORMATION: biomarker

<400> SEQUENCE: 18

| | |
|---|---|
| atgcgtgcga taattacgga tattcgagcg ggaaaggccg ccgcgctcgc ggaggacggc | 60 |
| acggttcacc ttgtagacgc gaagaacaga gcggtcggac aggagattcg gattccggcg | 120 |
| aagcgccgca gacggtggaa aaagccgctg acctgggcgg cgtgcgtggc tgtcctgtgc | 180 |
| ggcatggcga ccaccggcgt gtacgccgcg tatgagccgt atgccagcgt cagcgtcgtg | 240 |
| ggcggcacgg acagcgtgga gtatacggta accggttcg atcaggtgct cggcacccgc | 300 |
| gtttccggca gggagcagcc gccggacggc aaaattccgc ggtttgtaca cattgataag | 360 |
| gcggtggagc ataccgtccg gcaggaagca aggaaggcg agagcgtcag catcaccgtg | 420 |
| acctcgcgca gcagcggcca cgccgaacgg ctccgcgagc atatcgacga tcgg | 474 |

<210> SEQ ID NO 19
<211> LENGTH: 1302
<212> TYPE: DNA
<213> ORGANISM: Artificial
<220> FEATURE:
<223> OTHER INFORMATION: biomarker

<400> SEQUENCE: 19

| | |
|---|---|
| gtgaataaca agcggacttt cttcagtat gtgattccgt ccgtgttatc ctttgcgctt | 60 |
| tccggggtgt atgccatcgt tgacggtttc tttgtaggca actcaatcgg ggatgccgga | 120 |
| cttccgcaa tcaacattgc atatcccatc acggcggtcc tgcaatccgt agggacagga | 180 |
| atcggaatgg gtggttcagt caaatactcc attctgaaag cagcaggaaa tgagaaaaaa | 240 |
| gcacgggagt tcgttgccgg tgcaacatgg ctgatgcttc ttttcagcgc tgtcctgact | 300 |
| gtcaccgttt tcttcacttc agagaaaatc ctttctgccc ttggtgcatc gggcgagttg | 360 |
| cttactctgg gaaatgagta tatcaaggta attgcccttg gagcgatttt acaggtgttc | 420 |
| ggcaccggac tggttccgtt tatgcgtaat tacggcggtt cttgtgggc aatgatcgct | 480 |
| atgatctgcg gctttgctac caatgttgct cttgactata cttttgtgtg ggttcttgga | 540 |
| cggggcatgt acggtgcggc attggcgacc attattgggc agggagttac catggcggtt | 600 |
| gcactcgtgt attgcgccat caaaagaac ctcactctga aaatcgcacc tgttgatacc | 660 |
| ccgaaaacgg catttcagat attaaaaatc ggacttgctc catttggctt gaccccttgcc | 720 |
| ccaaatatct ctcttgtgat catcaaccga ttttcggttt attatggcgg acaggaggct | 780 |
| atcgccacct atgcctgtat ctcctatatc atctgcattg tttatcttct tttgcagggt | 840 |
| gtcggtgatg gtagccagcc gctcatgagt cagttctacg gagcaggcga agaaaaatcg | 900 |
| ctcaaacaaa ccaaaacgct ggcgtatgaa ttttccatgg ttttggcggt aatcagtgcg | 960 |
| attctgattt acctgctccg tggaaagatt ggactactgt tcggttcatc tgccgaggta | 1020 |
| aacgcagggg tcataaaggt catgccgatc ttccttgtgt cggttccgtt tgacgccatc | 1080 |
| acacgagttt ccgcggcggc tttctacgca accgaaaaaa gtgtgctgtc ctatgttctg | 1140 |
| acctttatcg aacccatcat catgctgtg ttgatgctga tgctgccgcc ggtgtttggc | 1200 |
| ggtcaaatca cgatttggtg gagcgccgta tttgcaaagg tcattaccgc atcagtaagc | 1260 |
| attgtgctgt ccgttagata cagcgcacaa agaaatcgat aa | 1302 |

<210> SEQ ID NO 20

<211> LENGTH: 648
<212> TYPE: DNA
<213> ORGANISM: Artificial
<220> FEATURE:
<223> OTHER INFORMATION: biomarker

<400> SEQUENCE: 20

```
aaaccgctgg aatattacac caacaacctg ggctgcactc tgacggtgct gagcgccatg      60
cgcaaataca atgtaaaaaa ctttgtgttc tcgtcctccg ccacggttta cggagacccg     120
gccagcgtgc ccatcaccga ggacttcccc accggcgcca ccaccaaccc ctacggcacc     180
accaaggtga tgatggagca gattttaaag gattactgca aggcggaccc cacgatgaat     240
gtggccctgc tgcgctattt caaccccatc ggcgctcatg aaagcggcct catcggcgag     300
gaccccaacg gcattcccaa caacctggtg ccctacatcg ccaaggtggc cgtgggcacg     360
ctggaaaagg tgcatgtgtt cggcaacgat taccccacgc ccgacggcac cggcgtgcgc     420
gattatatcc atgtggtgga cctggcccgc ggccatgtgg cggcgctgaa aaagctggct     480
tcgaactgcg gcctgttcat ctgcaacctg gcacggggac agggctacag cgtgctggac     540
gtcatcaaag catacagcaa ggcctgcggc aaggacctgc cctatgtcat cgacccgcgc     600
cgtcccggcg acattgccga atgctacgcg gaccccgcca aggcccgg                   648
```

<210> SEQ ID NO 21
<211> LENGTH: 279
<212> TYPE: DNA
<213> ORGANISM: Artificial
<220> FEATURE:
<223> OTHER INFORMATION: biomarker

<400> SEQUENCE: 21

```
caggaggtaa atgaaatgcc agaaaagaag tctgaaagac cagaaggtca gatgagaaga      60
agaccaatgc gcagaagaaa gaaagtatgt gcattttgtg ctgatgcaaa caaggcatta     120
gattataaag atgttgcttt attaaagaag tatgttctg aaagaggaaa gattcttcct      180
agaagaatta caggtaactg tgcaaagcac cagagagccc ttacagtagc tgtaaagaga     240
gctcgtcata ttgctttact tccatataca gtagaataa                            279
```

<210> SEQ ID NO 22
<211> LENGTH: 1755
<212> TYPE: DNA
<213> ORGANISM: Artificial
<220> FEATURE:
<223> OTHER INFORMATION: biomarker

<400> SEQUENCE: 22

```
atgaaatcaa agaaccgggg ggcaatccga cagctttta tgtttgttgg cagtagcaag       60
gggaaaatga attttccat tcttatggcc gttttagggg aactatttgg tatggttcca      120
ttccttatgc tggctatgtt ggcagattca ctctatttcg gaacagctac tactaaagat     180
acggtgatat tggcgggaat cgcggcactt tgccagtgca ttaagacatt ccttatatgg     240
aggtcgtccc ttctgtccca ccgtattcc tttactattt tacaaaatat acgtgaaaaa      300
attgccgata aaatggcgaa ggttcccatg ggcgtcatgt ggaaacccc ttccggcagt      360
tttaaaaact taattgtaga taatgtagca aagctagagg attctatggc ccatttatg      420
cctgaacttc cgtcccacat tacagcaccg ctatgcagta ttctattaat ctttatttg      480
gattggcgta tggggctggc ctctttaatt actgtcccgt gggaggttt gttttcgct       540
gccatgatgc gcggatatgc ctcccgtatg gaaaactata tgtgttctgc gaatgaaatg     600
```

```
aacagttctc ttgtggaata tgtaaatggt attcaggtca ttaaagcttt taaccggtcc      660
agctcgtcct atggtcaata ctcaaaagct gtcaattact tccacgactg caccatggaa      720
tggtggagcg agtgctggct atggaatgcg ccgctcgcg cagtccttcc ctccaccttta      780 cttggcacgt ttcctatcgg tgctttgctt tttatgaatg gttcgattac tttaccggtt      840
ctgatgatat gtcttattgt cccccttggc tttacagggc cgctgatgaa agtatcggaa      900
gccatggagc aggtgagtat gatcaaagga aaccttgaac aagttactgc cttcttaaaa      960
actcctgaac tgcagcggcc tgcggacccg ttactctca cagaaccgac atttgaattt     1020
agtcacgttt gctttggtta taacaaaagt gaagtgctgc acgatatctc atttaagacg     1080
tcaccgaaat caatgacagc gattgtcggc ccatccggat ctggtaaatc taccatagcc     1140
aaattaatgg cggggttttg gatgccacc tccgggactg tgcttttttgg ttcacaggat     1200 attcgcaaca tcccctttga gcagctgatg ggagaaatca gttatgttgc acaggataac     1260 tttcttttg ataaaaccat ccgtgataat atccgcatgg gaaatccagc cgcaacggac     1320
gaacaaatag aaaccgttgc aaaagctgca aactgccatg attttatcat gcaattagaa     1380
aaaggctacg acactatggc cggagatgcc ggagaccgcc tatctggtgg agaacgccaa     1440
cgtatcacca tagcgcgtgc catgctaaaa aaagcttccg tggttattct tgatgaagca     1500
actgcctatg cagacccgga aaatgaagca ctgatacaag aagcaatcag taagttaatt     1560
tccgggaaaa ccctaattgt tgttgcacat cgtctgaata caatccgcaa tgccgatcaa     1620
atccttgttg tagctgatgg gaaaatagcc ggatgcggaa cgcaaaatga actgttagag     1680
aactgccctc tttataagga aatgtgggag aattattcag atgcggtaac ttccaaaacg     1740
aaaggagaat cttag                                                      1755
```

<210> SEQ ID NO 23
<211> LENGTH: 1734
<212> TYPE: DNA
<213> ORGANISM: Artificial
<220> FEATURE:
<223> OTHER INFORMATION: biomarker

<400> SEQUENCE: 23

```
atgagtaagc tgaaagaaaa gttaatgctg tcggagaaag ctactccga cctgaaaaaa      60 gcgattacgg cctgcacaat caccaatatc gcgctgttgc ttccgtctat ggtagcctgc     120
ctgctctttt gggagttgtt aaagccattt actggagaag caatttcgtg ggccgcattg     180
tggaagctgc tgggcctagg gctggtggca gctattctgg tattcctggc cgcgaaaaac     240
gattatagga aaacctatat tgcttcctat aaggaggcca gcacgaccag acttcggatc     300
gcggagcatc ttcgcaagct ccccatgagc ttctttaaca caaagatttt gtccgatatt     360
accactaaca tgatggcgga ttgcagcagc atggaatcca tgctcagcag taccatcccg     420
ccgctgattc aaatatcat ctctgttacc ctgacctgcg ttttgtctgg attttttgac     480
tggagaatgg cccttgcgat tttctgcaca atgccggtta cattccttat catctggtgc     540
gggcgcaagc tacaacttcg tctgtttgac aaacaggtgg atgtgaaact ggaggcgtct     600
agccagattc aggaatacct ggaaggtatt aagatcatca atcttgtgg tcttggcggt     660 tcccgctttg atgcgttgga taaagcactc caggccatga aaaaatcgc cattaaagtg     720 gaactggcct ccgtattct ggttcaggga gccagcctga tcctgcaagc agggcttggc     780
attactattt tcattggaac ggtgctgata accggcggca aaatcgaatt gctccctctg     840
```

| | |
|---|---|
| ctggtgctgc tcatgttctc cacgcagatt tacggcccga tccttgccat tctctcacag | 900 |
| ttgacttctc tgtttcattt ggagactgtc accaaccgta tgcgtaccct gctgaccacg | 960 |
| cccgctatgg agggcgagga taaggatgta tccaagtatg acattgaact gaaaaatgtc | 1020 |
| actttcggat ataaccagga cgatgttatc aaggatgtgt cttttttctat tcctgctggc | 1080 |
| agcgtaatgg ccctggtagg gccttccggc agcggcaaaa gcacgatttc caaactgatc | 1140 |
| gcccgctttt gggatataag aaaaggccag atcaccattg gtggtatgga tgtcagcacc | 1200 |
| attgaaccgg aacacctgat gcgctgtatg tcctttgtat tccaggatgt gaccctgttc | 1260 |
| aacgatactg ttttttaacaa tatccgtgta ggtaacatga acgctaccga gaacaggtc | 1320 |
| atggcagcgg caaaggcagc gtactgtaac gaatttatcc agcgattgcc ggatggttat | 1380 |
| cagactatct gggggagaa cggcagcact ctttctggcg gagaacgtca gcgaatctcc | 1440 |
| attgcccgcg ctctgctgaa agatgccccg attattcttc ttgatgaagc aacagcatct | 1500 |
| cttgacccgg agaacgaggt tttaatccag cgggccattg caaagctggt ggagggtaag | 1560 |
| acggttatta tgattgctca ccggcttcgt accgttgtgg atgccgacca aattctcgtt | 1620 |
| cttgataacg gcagactggt ggaacacggt acacatgatg aattgatgaa aaagaacgga | 1680 |
| ttgtactata aactgttcca tatccaacag gagagtcttg gttgggctgt gtaa | 1734 |

<210> SEQ ID NO 24
<211> LENGTH: 1323
<212> TYPE: DNA
<213> ORGANISM: Artificial
<220> FEATURE:
<223> OTHER INFORMATION: biomarker

<400> SEQUENCE: 24

| | |
|---|---|
| atggaaaaat taaagagaag cagatggttc aatcggttaa atagcatgag tattaggatg | 60 |
| tcctttgttc tttatgcttt gttttcgttg ttgattggaa taattatttg tatactttta | 120 |
| atttcaatgg ttgacaaata cagaataaat ttgaactata gtatgaaaa tatgtcaaca | 180 |
| aggtatgata taccggaaaa tggttcattt accgccgctt atagtaatga ccaaacaaaa | 240 |
| tacacaatat ttgatacgaa aggaaacgag atatgcaagt tcaatgttga ttatcaaaaa | 300 |
| gaacgcccag tacacgaata tgtctatccg aaccatgttt catatatcga gtttcacct | 360 |
| aattttacaa accgggatag gcttattgac agtgttttag gttcattaaa tgttgcaatt | 420 |
| attcctatcg tattatctat taatatgata tgttgtgtaa cattttttta taaaaaaaaa | 480 |
| atatcgaaac ctattaagct attaactaat gcgtatcata aaattgaagc aaatgactta | 540 |
| gattttacgt tatcatatcc attaaatgat gaaatgggaa aactctgtca tgcctttgaa | 600 |
| aaaatgaaag actgtttggc gaaaaataat gaaactatgt ttcgacaatt tgctgaacag | 660 |
| cgccgtctaa acgctgcttt ttcacatgac ttacgcactc ctttgacttt actaaagggt | 720 |
| catgctacta tgctgctttc ctttattccc aaaggcttag tatcacaaga gaaatatta | 780 |
| gatgaaatat cagtaatgtc aaaaaatgtt tcacgtcttg aaaaatatgt aaatgctatg | 840 |
| acgaacttat ataggttaga ggatattgat attccacggc aacagattac atttcatgca | 900 |
| cttattgata ttttaataa cacagcagaa gcactttgtt atgacaaaca ttttcaatt | 960 |
| actacaagcg gtgataatat aaccttgttt atcaatttaa atacagtcat gcagatttat | 1020 |
| gaaaatttac tctctaatag tattagatac gcaaaaagtg atattgctat tagcgcagta | 1080 |
| atagagaata taatttagt tatatctgtt tcagatgatg gttgcgggtt taaaaatatt | 1140 |
| gatattgaaa aagcgacatt accattttat aaatcatcga agatatatc tactgaacat | 1200 |

```
ttgggattag ggctgaatat tagtaagatt ttaagtgaaa gacatggcgg aaatatccaa    1260
attgctaata acgaagcagg gggagcatgt gttacagtaa aaataaattg caatgaaagt    1320
tga                                                                  1323
```

<210> SEQ ID NO 25
<211> LENGTH: 3888
<212> TYPE: DNA
<213> ORGANISM: Artificial
<220> FEATURE:
<223> OTHER INFORMATION: biomarker

<400> SEQUENCE: 25

```
atgaataaaa tatactccct taaatatagt gctgccactg gcggactcat tgctgtttct      60
gaattagcga aaagagtttc tggtaaaaca aaccgaaaac ttgtagcaac aatgttgtct     120
ctggctgttg ccggtacagt aaatgcagca atattgata tatcaaatgt atgggcgaga     180
gactatcttg atcttgcaca aaataaaggt gttttccagc ccggagcaac agacgtaaca     240
atcactttaa aaacggaga taaattctct ttccataatc tctcaattcc ggattttct      300 ggtgcagcag cgagtggcgc agctaccgca ataggaggtt cttatagtgt tactgttgca     360
cataacaaaa agaaccctca ggccgcagaa actcaggttt acgctcagtc ttcttacaag     420
gttgttgaca gaagaaattc caatgatttt gagattcaga ggttaaataa atttgttgtg     480
gaaacagtag gtgccacccc ggcagagacc aaccctacaa catattctga tgcattagaa     540
cgctacggta tagtcacttc tgacggttca aaaaaaatca taggttttcg tgctggctct     600
ggaggaacat catttattaa tggtgaatcc aaaatctcaa caaattcagc atatagccat     660
gatctgttaa gtgctagtct atttgaggtc acccaatggg actcatacgg catgatgatt     720
tataaaaatg ataaaacatt tcgtaatctt gaaatattcg gagacagcgg ctctggagca     780
tacttatatg ataacaaact agaaaaatgg gtattagtcg gaacaaccca tggtattgcc     840
agcgttaatg gtgaccaact gacatggata acaaaataca atgataaact ggttagtgag     900
ttaaaagata cctatagtca taaaataaat ctgaatggca ataatgtaac cataaaaaac     960
acagatataa cattacacca aaacaatgca gataccactg gtactcaaga aaacataact    1020
aaagacaaag atattgtgtt cacaaatggg ggaaatgtcc tgtttaagga taatttggat    1080
tttggtagcg gtggtattat ctttgacgaa ggccatgaat ataacataaa cggtcaggga    1140
tttacattta aaggagcagg aattgatatc ggaaaagaaa gcattgtaaa ctggaatgca    1200
ttgtattcca gtgatgatgt tttacacaaa ataggccccg gtactctgaa tgttcaaaaa    1260
aaacaggggg caaatataaa gataggtgaa ggaaatgtta ttcttaatga agaaggaaca    1320
tttaacaata tacccttgc aagcggaaat ggtaaggtaa tactaaataa agataattcc    1380
cttggcaatg atcaatatgc ggggatattt tttactaaac gtggtggcac gctagattta    1440
aatggacaca atcagacttt tactagaatt gccgccactg acgatggaac aacaataact    1500
aactcagata caacgaaaga agccgttctg gcaatcaata acgaagactc ctacatatat    1560
catgggaaca taaatggcaa tataaaacta acgcacaata ttaattctca ggataagaaa    1620
actaatgcaa aattaattct ggatggtagt gtcaacacaa aaaatgatgt tgaagtcagt    1680
aatgccagtc ttaccatgca aggccatgca acagagcatg caatattcag aagcacagcg    1740
aatcattgct ccctggtatt tctttgtgga acggactggg tcaccgtttt gaaagaaaca    1800
gagagttcat ataataaaaa gttcaattct gatcacaaaa gtaataatca gcagacctca    1860
```

| | |
|---|---|
| tttgatcagc cagactggaa aaccggggtg tttaaatttg atacattaca cctgaacaat | 1920 |
| gctgactttt caatatcacg caatgccaat gttgaaggaa atatatcagc aaataaatca | 1980 |
| gctatcacaa tcggcgataa aaatgcttac attgataatc ttgcagggaa aaatattact | 2040 |
| aataatggtt ttgacttcaa acaaactatc agtactaatc tatccatagg agaaactaaa | 2100 |
| tttacaggtg gcatcactgc acataacagc caaatagcca taggtgatca agctgtagtt | 2160 |
| acacttaatg gtgcaacctt tctgaataat actcctataa gtatagataa aggagcaaaa | 2220 |
| gttatagcac aaaattccat gttcacaaca aaaggtattg atatctccgg tgaactgact | 2280 |
| atgacgggaa tccctgaaca gaatagtaaa actgtaacgc cgggtctcca ctacgctgct | 2340 |
| gatggattca ggctgagtgg tggaaatgca aatttcattg ccagaaatat ggcatctgtc | 2400 |
| accggaaata tttatgctga tgatgcagca accattactc tgggacagcc tgaaactgaa | 2460 |
| acaccgacta tatcgtctgc ttatcaggca tgggcagaga ctcttttgta tggctttgat | 2520 |
| accgcctatc gaggcgcaat aacagccccc aaagctacag ttagcatgaa taatgcgatc | 2580 |
| tggcatctaa atagccagtc atcaattaat cgtctagaaa caaaagacag tatggtgcgt | 2640 |
| tttactggtg ataatgggaa gtttacaacc cttacagtgg acaaccttac tatagatgac | 2700 |
| agtgcatttg tgctgcgtgc aaatctggcc caagcagatc agcttgttgt caataaatcg | 2760 |
| ttgtctggta aaacaaccct tctgttagtc gacttcattg agaaaaatgg aaacagcaac | 2820 |
| ggactgaata tcgatctggt cagcgcacca aaaggaactg cagtagatgt ctttaaagct | 2880 |
| acgactcgga gtattggctt cagtgatgta acaccggtta tcgagcaaaa gaacgataca | 2940 |
| gacaaagcaa catggactct gatcggctat aaatctgtgg ccaacgccga tgcggctaaa | 3000 |
| aaggcaacat tactgatgtc aggcggctat aaagccttcc ttgctgaggt caacaacctt | 3060 |
| aacaaacgta tgggtgatct gcgtgacatt aacggtgagt ccggtgcatg ggcccgaatc | 3120 |
| atgagcggaa ccgggtctgc cggcggtgga ttcagtgaca actacaccca cgttcaggtc | 3180 |
| ggtgcggata caaacatga actcgatggc cttgacctct tcaccggggt gaccatgacc | 3240 |
| tataccgaca gccatgcagg cagtgatgcc ttcagtggtg aaacgaagtc tgtgggtgcc | 3300 |
| ggtctctatg cctctgccat gttgagtcc ggagcatata tcgacctcat cggtaagttc | 3360 |
| gttcaccatg acaacgagta taccgcaact ttcgccggcc ttggcaccag agactacagc | 3420 |
| tcccactcct ggtatgccgg tgcggaagtc ggttaccgtt atcatgtaac tgactctgca | 3480 |
| tggattgagc cgcaggcgga acttgtttac ggtgctgtat ccgggaaaca gttctcctgg | 3540 |
| aaggaccagg gaatgaacct caccatgaag gataaggact ttaatccgct gattgggcgt | 3600 |
| accggtgttg atgtgggtaa atccttctcc ggtaaggact ggaaagtcac agcccgcgcc | 3660 |
| ggccttggct accagtttga cctgtttgcc aacggtgaaa ccgtactgcg tgatgcgtcc | 3720 |
| ggtgagaaac gtatcaaagg tgaaaaagac ggtcgtatgc tcatgaatgt tggtctcaac | 3780 |
| gccgaaattc gcgataatct tcgcttcggt cttgagtttg agaatcggc atttggtaaa | 3840 |
| tacaacgtgg ataacgcgat caacgccaac ttccgttact ctttctga | 3888 |

<210> SEQ ID NO 26
<211> LENGTH: 447
<212> TYPE: DNA
<213> ORGANISM: Artificial
<220> FEATURE:
<223> OTHER INFORMATION: biomarker

<400> SEQUENCE: 26

| | |
|---|---|
| atgaacttaa gtaatttaaa acctgcagag ggatctacta aaacaagaaa aagaatcgga | 60 |

```
cgcggtccgg gttctggttt gggaggtact tctaccagag gtcataaggg agctaaatca      120
agatctggtt attctaagaa aataggtttt gaaggtggcc agatgcctct ccaacgtcgt      180
gttcctaaat tcggttttaa gaacattaat cgtgtagagt ataaagctat caacttggat      240
acaattcaga aacttgctga agctaaaaag ttggagacag ttggtattaa tgattttatc      300
gctgctggct ttatttcttc aaatcagttg gtaaaagtat taggtaatgg aactttgact      360
acaaagttgg atgtgcaagc tcatgcattc tctaagactg ctgttgctgc cattgaagct      420
gctggtggaa gtgtagtaaa actctaa                                         447
```

<210> SEQ ID NO 27
<211> LENGTH: 1920
<212> TYPE: DNA
<213> ORGANISM: Artificial
<220> FEATURE:
<223> OTHER INFORMATION: biomarker

<400> SEQUENCE: 27

```
atgaacatta tcaatatcgg gattcttgcc catgtagatg cgggcaagac gacactgaca       60
gaaagcctgc tgtatgccag cggagccatt tcagagccgg ggagcgtcga aaaagggaca      120
acgagaacgg acactatgtt tttggagcgg cagcgtggga ttaccattca acggcagtc      180 acttcttttcc agtggcacag ttgtaaagtc aatattgtgg atactcccgg ccacatggat     240
ttcttggcag aggtataccg ctctctggct gttttggacg gggccatctt ggtgctctcc      300
gctaaagatg cgtgcaggc ccagacccgt gttctgttcc atgccctacg gaaattgaac       360
atccccacca ttatctttat caacaagatc gaccaggttg cattgatttt ggagagcgta      420
tatcagtctg ttcgggataa gctctccgct gatattatca tcaagcagac agtgtcgctg      480
tcctcgaaaa taactctgac agaaaacact agtgcagagg tgtgggattc ggtcatcgaa      540
aataacgatg agttattggc aaagtatatc gcaggagaat caatcagtca gaaagaactt      600
gcgcaagaag aacagcggcg agttcaagac gcctccctgc tcccggtcta tcatggtagc      660
gccaaaaacg gccttggcat tcaacagttg atggatgcgg tgatagggct gttccaatcg      720
accaaggaac aggggagcgc cgccctgtgc ggtagagttt taaggtgga gtatacagat       780 tgcggccaga ggcttgtcta tctgcggcta tacagcggaa cgctgcgtct gcgggatacg      840
gtggccctgg ccgggagaga aaagctgaaa atcacagaga tgcgtattcc atccaaaggg     900
gagattgttc ggacagacac cgcccataag ggcgaaattg tcatccttcc cagcgacagc      960
ttgagattaa acgatatatt gggggacaaa acccaacttc ctcgtgaaat gtggagtgat     1020
gttcccttcc ctatgctgcg gacgacgatt acgccaaaaa cggcagagca aagagaccgg     1080
ttgctggacc tccttacgca aattgcggat actgaccccg ttttgcacta cgaggtggat     1140
tccaccaccc atgagatcat tcttttcttttt ttgggtcgga tgcagttgga ggttgtttcc    1200
gctttgctga cggaaaaata caagattgaa acagcagtga aggaacccac cgtcatttat    1260
ttagagcggc cgctcaaagt ggccagtcac accatccata tcgaggtgcc gcctaacccg     1320
ttttgggcat ctatcggact gtctgttaca ccgctcccgc ttggctccgg tgtaaaatac     1380
gagagccggg tttccctggg atacctgaac cagagttttc aaaacgctgt catggatggt     1440
atccgttacg gtttggggca aggcttgtgt ggctggaacg taacggactg taagatttgc     1500
tttgaatacg gactttacta tagcccggtc agcacgccgg cggacttccg ctcattggcc     1560
ccgattgtat tggaacaggc attgaaggaa tcggggacgc agctgctgga accttatctc     1620
```

-continued tccttcatcc tctatgcgcc ccaggaatac ctttccaggg cttatcatga tgcgccgaaa    1680
tactgtgcca ccatcgaaac ggcccagata aaaaaggatg aagttgtctt tactggcgag    1740
attcccgccc gttgcataca ggcataccgt actgatttgg ccttttacac caacgggcgg    1800
agcgtgtgcc tgacggaact gaaagggtat caggccactg tcggcgagcc agtcatccag    1860
ccccgtcgtc caaacagccg tttggataag gtgcgccata tgttcagtaa gattccttga    1920

<210> SEQ ID NO 28
<211> LENGTH: 162
<212> TYPE: DNA
<213> ORGANISM: Artificial
<220> FEATURE:
<223> OTHER INFORMATION: biomarker

<400> SEQUENCE: 28
attttatttt catctttaat atgtctgttt gtttattgga agaaaaaac aatagaagaa      60 ctggtctcta tcaccggctt gaccgcctcg aatattaaag tcaagctaca tcgcatccga     120
aaaaaattgt ttgtattatt aaatggaatg gatcatgagt aa                        162

<210> SEQ ID NO 29
<211> LENGTH: 240
<212> TYPE: DNA
<213> ORGANISM: Artificial
<220> FEATURE:
<223> OTHER INFORMATION: biomarker

<400> SEQUENCE: 29
atgacatcgc ttttttgttg tgacccggga gggattcaaa ccctcgacct tcagaaccgg      60
aatctgacgc tctattcact aagctaccag gccaaagacg gggcaaaagt aaatataata    120
tcggaggaaa gcaaatgtat tgaggatgag ttttcatatt cttctttttt tctgccgaaa    180
aacataactt ctgatatttt gcaactctct ttagcggata tactgccatt ttgcaaataa    240

<210> SEQ ID NO 30
<211> LENGTH: 510
<212> TYPE: DNA
<213> ORGANISM: Artificial
<220> FEATURE:
<223> OTHER INFORMATION: biomarker

<400> SEQUENCE: 30
gtgcttctgc aagcctggag gccgcctgaa gtcattgatc aggatgccgt gtttgctttc     60
ggtgagacct acgatgaagt catcagaacc agagtctttg aagatttcta cagggaacag    120
gacatccggc cctgggtgtg taataaggca gatccagaaa gcaagggccc gattgagaac    180
tccattgggt tcatgaagaa aaaattcgtc agtgcgcgga agtcacctg tatcgatgat    240 gtatggcgct cccttcccat atggctggac ggaaaaagcg gcactgctgc ccttttttcc    300
atcagtatac gaaacatccc cgaatcattc catcgggtga gcgcaatgac ggataatgag    360
aaaacgaccg ccctcatccc atctgttggc gcagatggag ggcagccgcc tcacaattca    420
actaaacaga ggataccaca tgaaacctgc gaaagcaatc cttcggagga aaatattgag    480
gaaatgcgtg agagaatctc accacaataa                                     510

<210> SEQ ID NO 31
<211> LENGTH: 132
<212> TYPE: DNA
<213> ORGANISM: Artificial
<220> FEATURE:
<223> OTHER INFORMATION: biomarker

<400> SEQUENCE: 31

```
gtgaagaatg gagatacttt ttctgtttac ggcaaagagt atgccattga cagcagtggg      60
catatcaatg tttcggcaga agatgaattc acatcgacag aaattaaata tccaagccgt     120
tcaatacaat ag                                                         132
```

<210> SEQ ID NO 32
<211> LENGTH: 897
<212> TYPE: DNA
<213> ORGANISM: Artificial
<220> FEATURE:
<223> OTHER INFORMATION: biomarker

<400> SEQUENCE: 32

```
gtgtcggaat tggataagaa aaagaaatta ctatcaaaaa agctggcaaa aatacgtgga      60
tggatacagg ccgcagcaac gctgctgacc aatattcata ttccaaattt atttaagggt    120
aaaatatatc agggcaatgc aaaaacagta tgcgtacccg gattaaactg ctactcctgc    180
cctgccgcga caggagcctg tccaataggg gcatttcagg cagtcgtcgg atcatcaaga    240
tttaagtttt catactacat aaccggattt tttattttac tcggtgtaac tctcggcaga    300
tttatatgtg gtttttttgtg cccatttgga tggtttcagg atttacttca taaaatcccc    360
ggaaagaaat tatccacagc caaactaaag cctcttaggt acctaaaata tgtcattctt    420
attgttttcg ttatacttct tccgatgctt gtaacgaact ctataggaat gggagacccg    480
ttcttctgca aatatatctg tcctcagggt gttttagagg gtgctatacc gttatctatt    540
ggaaatgctg ctatccgttc tgcgctggga aagctttttt ctttcaagtg tatgatttta    600
attgcagtga ttgtactaag tatcttattt tacaggccct tctgtaaatg gatttgtccg    660
cttggagcaa tctactcatt atttaataag gtcagcctgc tcaaaatcac cgttgatagc    720
aacaaatgtg tcggatgcgg tcaatgctca aaggcatgta agatggatgt ggatgtgtgt    780
aagacaccgg atcaccccga gtgcatacgc tgcggtgcct gcataaaggc ctgtccgaag    840
gacgccatct gctaccggtt tatgggaaaa tcatgtcaaa aaaatgacaa cagatag       897
```

<210> SEQ ID NO 33
<211> LENGTH: 174
<212> TYPE: DNA
<213> ORGANISM: Artificial
<220> FEATURE:
<223> OTHER INFORMATION: biomarker

<400> SEQUENCE: 33

```
gaaacggaga gcagattgat attgtttaat tttgagggcc ctgaaaaggg aactcagaaa      60
agcgaaacct tatgcgaaga gcgtgggggt gtagctcagc tgggagagca cctgctttgc    120
aagcaggggg tcaggagttc gagcctcctc atctccacca atttgggctc atag          174
```

<210> SEQ ID NO 34
<211> LENGTH: 720
<212> TYPE: DNA
<213> ORGANISM: Artificial
<220> FEATURE:
<223> OTHER INFORMATION: biomarker

<400> SEQUENCE: 34

```
ggaaaacata atcatcaatg tgtaaaatgt gatagtcatg aggaaaaaac gagagtcaca      60
gaaaggatgt gggaggcatt gtgcgggaag aggatcaaac aaccagcagc cttggctgta    120
```

| | |
|---|---:|
| ttatttgttc taatgtttat tggtggatgt ttttttgtga aagccaatca ggcaaaggaa | 180 |
| tttgagaaaa aagattatgg ggtgttttta aatgcggacg cctcatcttt ggaacgattt | 240 |
| aaaatgtatg aaacgattgt aattgatgca cagtatttta caaaagggga tattgaattg | 300 |
| ctccatcaaa atggaacagt cgtatataca tatctaaata ttgggtcgat tgaaaacttc | 360 |
| agggagtact atacaaccta tgcggaactg gcaatcggtg agtatgagca ttgggaggaa | 420 |
| gaacaatggg tggatgtagc aaacccagac tggcagaagt ttataggaca gctttctcag | 480 |
| aaactatatg aaaaaggtgt tgatgggttc tttatagata attgtgatgt atattattac | 540 |
| gctccacgcg agagtatttt tgaaggtctt acagctattc tgcaaatatt tggaagcgtg | 600 |
| caaagcagat ggaatggaag tatatctgtt ggaatataca acgaacccaa aactaatcca | 660 |
| aaaaataaaa gaatactgca aggagcaaga cttccatttt tatatttcca gttcccttga | 720 |

<210> SEQ ID NO 35
<211> LENGTH: 480
<212> TYPE: DNA
<213> ORGANISM: Artificial
<220> FEATURE:
<223> OTHER INFORMATION: biomarker

<400> SEQUENCE: 35

| | |
|---|---:|
| atgaccggct gcaaggggta tggcctccgg ggaagtgacg ccacgacaga aatcgagcgc | 60 |
| accaaagagg ccgatacgcc gggagaaatt ccgggcagga gcggcttgca ggcagaccgg | 120 |
| cggacagaaa caagtttatc atgcggggcg catggctccg cagcaaagaa atggaggaat | 180 |
| atcattatga aactgagcat gaaagaaaag aagattctct acgcttacgg ctgtcccagc | 240 |
| caccacaata cggtgacacg gctgaaatgg ctgacggccc tgacggttga cccggaggcc | 300 |
| aaacgccgca tgctggggtt ggcccgtaag gtggagacgg aggtggacga aagctggtac | 360 |
| gaggattttt accaccatct gcgcatggag atggacgagt accgccgtct aaagcgcagc | 420 |
| ctgcgagtgc tgaaatctta cactgattat gaggaggatt tatatgagga agctgtctaa | 480 |

<210> SEQ ID NO 36
<211> LENGTH: 933
<212> TYPE: DNA
<213> ORGANISM: Artificial
<220> FEATURE:
<223> OTHER INFORMATION: biomarker

<400> SEQUENCE: 36

| | |
|---|---:|
| atgcagacaa caaagaaaat gccgtcactg atattcatcc ttgtgggtgc agtgttagca | 60 |
| gggtatcttg gttatctgat aaatggtgcg tggacggaag ggattgcctt taatgaattt | 120 |
| atggacagat tcaatgaggt atgtgctgtt ccttttgcca attattacaa ttccaataca | 180 |
| gtaaaagcag tagccattgc attaggtatc tatgcgatgg ctattgtcat gtattacacc | 240 |
| agtcagagaa actatatgcc tggcaaagaa tttggtacgg caagatttga aaatccgaag | 300 |
| caggtcaaca agatacttgc agataaggat gaaaatttca accggatact cagccagaat | 360 |
| gtgaagatgt cgctggattt caggagactc aagctcaatg gaaatatcct tatctgtggt | 420 |
| ggttccggag caggaaaaac attttatgaa gtaaagccga atctgatgca gatgccgcat | 480 |
| aactgttcct ttatctgtac cgatccaaag ggagaaatcc ttagaagctg cgggcagatg | 540 |
| ttaaaaaata cggatataa cctgaaagtc attaatctgt tagagatgga taaatcagac | 600 |
| tgttacaatc cattttccta tatcagagag gaaacagatg tggtcaagct gattacaaac | 660 |
| cttatcagca atacgacacc aaagggagcg acaccaagtg atccgttctg ggaaaaagcg | 720 |

```
gaaggattgt tcttacaggc tatctttat tatgtgtggc tggaggtaca gccggcaaag      780
agaaactttg agacagtact taaacttctt ggagaggcag aggttacaga gcagggaag      840 gcatcaaagc tggatgtgcg tatgaagttt ttagaggaag ttccccactc ggagccaatc    900
atccggcagt caagcagtac aacaaatgta tga                                 933

<210> SEQ ID NO 37
<211> LENGTH: 117
<212> TYPE: DNA
<213> ORGANISM: Artificial
<220> FEATURE:
<223> OTHER INFORMATION: biomarker

<400> SEQUENCE: 37
atttgtagtt tcatggtttc tgcattcttt cttttgggta gtaaaggtat ggtttttatc     60
atactcaata gtataataaa tgtaaaaatg actggtttaa acgttggttt agactag       117

<210> SEQ ID NO 38
<211> LENGTH: 426
<212> TYPE: DNA
<213> ORGANISM: Artificial
<220> FEATURE:
<223> OTHER INFORMATION: biomarker

<400> SEQUENCE: 38
ttggtagcca tatccttacc tttaccgctg gagcgttatg cagatatcgg catatggcag     60
atcgaggttt tcttcaaaac ctgtaaatcc atgctgaacc tgattggaga atgccacagc   120
ttatcttatg atgcactgac agcccatgtg gccattgtgt ttaccagata tatgttactt   180
gcaatggagc aacgtcaaaa tgaagatcag agaacgcttg ggaagttgtt cttccttctt   240
gtcgatgaaa tggcagatat tactttcaac agatcacttg gtattctgat ggctgcctta   300
atggcaagcc ttcaggaaat cttaaagctc agtgacgaac aactgactgc ttttactgct   360
gattttgaag caagattacc agaatatctg cgcaatgcac tccacccaga gattgcaatg   420
gcataa                                                              426

<210> SEQ ID NO 39
<211> LENGTH: 669
<212> TYPE: DNA
<213> ORGANISM: Artificial
<220> FEATURE:
<223> OTHER INFORMATION: biomarker

<400> SEQUENCE: 39
gatgcggcgg caaaggcagc aggaaatgta gcagtgatct ccgcaggctg ggatccgggc     60
atgttctcct taaatcgtgt atacgcaaac gcaattctcc cggatggtaa agactataca   120
ttctggggca aggcgtaag ccagggacat tctgacgcga tccgccgcat tgatggcgtg    180
aaggacgcaa acagtatac agtcccggtt gagagcgtgt tagagaagat cagaaacggc   240
gagaccccgg aactcacaac gagagagaaa cacacgagag agtgctatgt tgttgctgaa   300
gagggtgctg atcttgcgcg tatcgaaaaa gagatcgtaa cgatgccgaa ctacttctcc   360
gactatgata caacggttca tttcatcagc gaggaagaga tgaagcgtga ccattccacg   420
cttccgcacg gcggtttcgt gatcagaaac ggaaagaccg gatggaatca ggagaataca   480
catgtgatcg agtatcgtct gaaactggat tccaacccgg agttcacttc ctccgtgatc   540
gtttgctgtg cccgtgccgc attccgcatg aagcaggagg gaatgagcgg atgcaagacc   600
```

```
attcttgaca ttccgccggc atacctttcc gcaaagagcg gcgaggaact cagaaagaat      660
ctcctgtaa                                                             669

<210> SEQ ID NO 40
<211> LENGTH: 759
<212> TYPE: DNA
<213> ORGANISM: Artificial
<220> FEATURE:
<223> OTHER INFORMATION: biomarker

<400> SEQUENCE: 40
cgtgcgaatc aggaagtgga agatcgtgtc atggactcca atgatatcga gcgtgagcgc       60
ggaattacca tcctttccaa gaataccgct gttttttata aagagaagaa gatcaatatc      120
atcgacaccc caggacatgc agatttcggc ggcgaggttg agcgagttct gaagatggta      180
aacggcgtta tcctggtcgt agacgcttac gagggtccga tgccgcagac caaattcgtt      240
ctgcagaagg ccctggaact ggatctgtcc gttatcgtct gcatcaacaa gatcgaccgc      300
ccggaggcaa gaccgactga ggtgatcgac gaggtattag aactgttcat ggatctggac      360
gcttctgacg agcagttaga ctgcccgttt gtatttgcat ctgcccgtgc cggcttcgca      420
aagaaagagc tggacgatcc ggaagtagat atgagcccgc tgtttgagac tatcgtcaat      480
tatatcccgg ctccggaggg agatccggac gcagacaccc agatgctgat cagcaccatc      540
gactacaacg agtttgttgg ccgtatcggt gtcggcaaga tcgacaacgg aagcctgaag      600
gtaaaccagg actgcgtgat cgtaaaccat catgatccgg ataagatgcg cagagtcaag      660
atcggtaagc tgtaccagtt tgacggctta aaacgtgttg aggtccagga agcaaccatc      720
ggtgatatcg ttgcggtatc cggcattgca gatctgcat                            759

<210> SEQ ID NO 41
<211> LENGTH: 429
<212> TYPE: DNA
<213> ORGANISM: Artificial
<220> FEATURE:
<223> OTHER INFORMATION: biomarker

<400> SEQUENCE: 41
gatgcaacca cggtattaag ccgtgccatt gtagagcagg gtatttaccc ggcagtagac       60
ccgctggagt ccacctcccg catcctcgac ccacgtgttg taggtgagga gcattacaag      120
gtagcccgcg gcgtgcagga ggttttgcag aagtacaaag agctgcagga tatcatcgcc      180
atgttaggta tggatgagct ttccgaggaa gataagctga ccgtatcccg cgcacgtaag      240
atccagagat tcttatctca gccgttcttc gtagcaggac agtttaccgg tctggaaggc      300
cgttatgtac cgttgagcga gaccattcag ggcttcaagg agatcctgga aggtaagcat      360
gatgacattc cggagcagta tttcctgaat gcaggtaata tcgatgacgt tcttgcccgt      420
gtgaaatag                                                             429

<210> SEQ ID NO 42
<211> LENGTH: 1794
<212> TYPE: DNA
<213> ORGANISM: Artificial
<220> FEATURE:
<223> OTHER INFORMATION: biomarker

<400> SEQUENCE: 42
atggcaattg aatttggttc ccgcagagag acctttgaga atttcaaggt ctacgaaacc       60
atgctggcag gccgcccgtt caaggtcgag atgggcaaga tgtgcggcct gtccaacgcc      120
```

```
agcgccatga tccgctacgg cgagacctgc gttctgtgca atgtcgtcat gagccccaaa    180
ccccgcgaag gcgtggattt cttcccgctg aacgtcgagt atgaggaaaa gctctacgcg    240
gcaggccgca tccccggcag ctttatgcgc cgcgagggac gccccggtga gcgcgccatc    300
ctgaccagcc gcgtggtgga ccgccccatg cgcccgctgt tccccaagga gatgcgcaac    360
gacgtgtgca tcaccatgac cgtcatgagc cttgacccgg actgcagccc cgagatcgcc    420
ggtatgatcg gcgcttctct ggtgactgct gtgtccgaca tccctggaa cggccccatc    480 ggcggcgtgc aggtgggtct ggtagacggc gagatcgtgc tgaaccccac ccaggagcag    540
cgcaaggtga gcgaccttgc cctgaccgtt gccgctacca tggacaagat cgttatgatc    600
gaggccggtg ccaacgaggt ggacgaggac actatgctca aggccatcaa gaccgcccat    660
gtggagatca agaagaccat cgagttcatc aacaagatcg tggccgagcg cggcaagccg    720
aagatcgact tccaggtcgt gggtctggat atggacgtgt ccacgccat ccagaacaag    780 tatctggacg acttcaaggc cgccatggac accgacgaca gaacgtgcg tgatgccgct    840 ctgctgccca ttatggacaa gatcgccgag gagtacccg acctgactgc cgccgatctg    900
gatctggtga gctacaagat gcagaagttc gtcgtgcgcc gctggctgct ggacgagggc    960
aagcgcgtgg acggccgcgg catcaacgag atccgcccgc tggctgccga ggtgggcatc   1020
ctgccccgcg tacacggctc cggcatgttc cccgcggtc agacccaggt gctgaccacc   1080
tgcacgctgg gcggcaccaa ggacaaccag ctgatggacg acctgaccga cgagcagacc   1140
aagcgctata tccatcacta aacttcccg ccgtactcgg taggcgaggc ccgcgcaccc   1200
cgcagccccg gccgccgcga gatcggccac ggcgctctgg cagagcgtgc tctggtgccc   1260
gtgctgccct cgctggaaga gttcccctac accatccgct gcgtgtctga ggtgctgtct   1320
tccaacggct ccacctcgca ggcttccatc tgcggctcca cgctggctct gatggacgca   1380
ggtgtgccca tcaaggcacc cgttgccggc atctcctgcg gcctgatcac cgagggcgac   1440
cgctggatga ccatgctgga cattcagggc gtggaggact ccacggcga tatggacttc   1500 aaggtcggcg caccgtaa ggcataccc gccatccaga tggacatcaa gatcgacggc   1560
ctgacctacg atatcatcgc agaggccttc gagaagtgcc gcaagggccg cctgtatatt   1620
ctggatgaga tcatcaagcc ggtgatcgca gagcctcgcc atgagctgag ccgctacgct   1680
cccaagatgt tcagcatgat gatccccacc gacaagatca aggacgtcat cggcaagggc   1740
ggcaaggtca ttcaggacat ctgcgccacc tgcaactgca agatcgacgt gcag         1794

<210> SEQ ID NO 43
<211> LENGTH: 1506
<212> TYPE: DNA
<213> ORGANISM: Artificial
<220> FEATURE:
<223> OTHER INFORMATION: biomarker

<400> SEQUENCE: 43
atggcagcgc cgcgcaccta tctggcaatc gacctgaaaa gcttctatgc ctcggtggag     60
tgcgtagacc gccatctgga ccccctgacc accaatctcg tagtggcaga tgcctcccgc    120
accgagaaaa ccatctgcct tgcggtgtcg ccctccctga aggcctacaa gatacccggc    180
agagcacggc tgtttgaagc cgttcagcgg gtgaaagagg tcaacgccca gcggctgcaa    240
actgccatcc ggcagaaaaa agcagtccgg ggagaggacg gcaaatacca ctttgccaga    300
acctctttcg atgccaacgc cctgaacgca gaccctgcac tggggttgag ttacattgtt    360
```

| | |
|---|---|
| gcgccgcccc ggatgcagcg gtatctggac gtttccaccc agatctacaa gacctacctc | 420 |
| aaatatgcgt ccccggcgga tatctacccc tactccattg acgaggtttt cattgatgtg | 480 |
| acgggctatc tgccctatta ccacatgagc gcccatgagc ttgccatgac catggtgcgg | 540 |
| gaagtgctga ccaacaccgg catcacggca acggcaggca tcggcaccaa cctctacctt | 600 |
| gcaaagctgg ccatggacat cgtagcaaag cacatcccgg cagacaaaga tggtgtccgc | 660 |
| attgcggagc tggacgagca gtcctaccgg tatctgctgt ggaaccatcg cccgctgacc | 720 |
| gatttctgga tgaccggtcc cggcaccgtc aagcggctgg aagcccacgg catttatacg | 780 |
| atgggggact ggcacggtt ttccatccac ggagaagatc gactgtatga dttttcggc | 840 |
| gtggatgcag aaattctcat tgaccacgca tgggctacg aaccctgcgg tatggagcag | 900 |
| atcaaaagct acaagcccag caccaacagc atcagcgagg acaggtgct gacctgccct | 960 |
| taccccaacg ataaagcaaa gctcatcgtc cgggaaatgg cagaaatctt gatgttccgg | 1020 |
| ctcaccgaaa agaagctggt gacggaatcc atcaccttgg agatcggcta cgaccgggag | 1080 |
| aacgtggacg agggcggcta ccgtggtctg acccagaccg accgctacgg cagaaccatc | 1140 |
| cccaaggcag ctcacggcac tatccggttt gatgccccca ccaatctggg cagcaccctc | 1200 |
| atcaacgaaa gcgcaaagct gttgagcgc atcaccgacc cggcgctgac ggtgcggcgc | 1260 |
| attaccatca acgccaacaa ggtcacgccg gacgagggca tctatcaggt ggactttttt | 1320 |
| accgacacca agaagctgga aaaggagaaa aaactccagc aagccatgct gggcatcaag | 1380 |
| aacaagtacg gtaaaaacgc cgtgctgaaa gccagcagct acgaagaagg tgccaccatg | 1440 |
| cgacagcgca acgcacaaat cggcgggcat agtgcgggag gttcagatgg aaaactacaa | 1500 |
| aaatag | 1506 |

<210> SEQ ID NO 44
<211> LENGTH: 864
<212> TYPE: DNA
<213> ORGANISM: Artificial
<220> FEATURE:
<223> OTHER INFORMATION: biomarker

<400> SEQUENCE: 44

| | |
|---|---|
| tcggcagcca acctgtccta tccgtccgga agcgcagagt ccggcaacct ggacttatcc | 60 |
| gtgtctacgt taacgcagca tgacacgctg gatgagctgc tggaaatgcc gatcacggta | 120 |
| tccggaaaca agatcattta cctggaagat atcgcagtgg tttcctacgc ggaggagcag | 180 |
| aagggcggcg tctcccgtta caatggtgaa gagaccatct ccatttccct gaccaagcag | 240 |
| cagagcagca ccgccatgga tttgtccaag caggtgcaga aggtcatcaa aagcctgcag | 300 |
| aatgatgatg atgaccctgac catcaccgta gcaagagatg aggcagactc catccaggac | 360 |
| tccttaaagg atgtagcaga gaccatggtg atggcggtcg tgatttccat gatcatcatt | 420 |
| ttcctgtttt tcggagattt caaggcatcc atgatcgtcg gaagctctat cccgaccctct | 480 |
| atcctgatgt ccctgatcgt tatgacgcgg gcgggattta cgctgaacat cattaccatg | 540 |
| agcggtctgg tcctcggtgt cggcatgatg gtagataact ctattgttgt gctggagagc | 600 |
| tgctttaggg ccatggataa gcagcaggat aaggggcac tggggtacgc gaaggcagcc | 660 |
| ctggaaggaa ccaacattgt ggtggcttcc atctttggct ccacggtaac cacctgtgtt | 720 |
| gtatttatcc cactggtatt cttgaacggt atgagcggcc agatgttcgg agccatgggc | 780 |
| tacaccatcg tattctgtat gtgtgcgtcc ctgctttctg caatcgccat cgtgccgctg | 840 |
| tgctatatga tgtataagcc gaag | 864 |

<210> SEQ ID NO 45
<211> LENGTH: 270
<212> TYPE: DNA
<213> ORGANISM: Artificial
<220> FEATURE:
<223> OTHER INFORMATION: biomarker

<400> SEQUENCE: 45

```
atggaacgtg tagtaatcac cggcatgggt gccatcactc cggtcggcaa cgatgtgccg      60
tcgttttggg agtcgctcaa gaccggcaag tgcggcatcg gtcccatcac caagtttgat     120
gtatccgatt ttaaggtaaa gctgggtgca gaggtcaagg acttcgaccc gacccagtat     180
atggagaagc gtgaggcgcg ccgcgcagat gcaaatgtgc attacgcaat ggcggcagcg     240
atccaggctg tcgagcaggc aggcctcaag                                      270
```

<210> SEQ ID NO 46
<211> LENGTH: 195
<212> TYPE: DNA
<213> ORGANISM: Artificial
<220> FEATURE:
<223> OTHER INFORMATION: biomarker

<400> SEQUENCE: 46

```
atgataaaaa actccttcca tgaatacttg aactcaaaag ctttctgtgc ctttgttatt      60
atattaacaa atccgaaggg caaaagaaa gttacagaaa aggccaaatg taacacttca      120
aggaaaatcg acatattgca aagaaagac atagaaaaat tatgcaaaat aacaatagat     180
caggacagca gatga                                                      195
```

<210> SEQ ID NO 47
<211> LENGTH: 126
<212> TYPE: DNA
<213> ORGANISM: Artificial
<220> FEATURE:
<223> OTHER INFORMATION: biomarker

<400> SEQUENCE: 47

```
atgcgagctg cagatacagg cacagaaaat ggcggatcag ttcatggatt taaagacgaa      60
aatgtccgaa aaaccctgat tttactgaaa aaatcaacag attacaggat gttacaattg     120
aaataa                                                                126
```

<210> SEQ ID NO 48
<211> LENGTH: 183
<212> TYPE: DNA
<213> ORGANISM: Artificial
<220> FEATURE:
<223> OTHER INFORMATION: biomarker

<400> SEQUENCE: 48

```
gtaataccgg tgcaagcctc tgcagcggaa ggattaataa gcaagccggc aatcgcaaat      60
aaaataaaga aatatctcat aaacatcatt tttgataaaa acaagcgaca ggagaaggtt     120
gttttcaaga tttcaagact ttttgtatg tttgcggtca ttttatcaaa aagtataata     180
tga                                                                   183
```

<210> SEQ ID NO 49
<211> LENGTH: 666
<212> TYPE: DNA
<213> ORGANISM: Artificial
<220> FEATURE:

```
<223> OTHER INFORMATION: biomarker

<400> SEQUENCE: 49
atgatcttgg atattaagag aaagaaaaaa gaaaaacgaa tccagctgtt cggtgctctg      60
attggaatcg gtgtggctgt agtctctccg ctttatttct tccacgcaga aaaagcagaa     120
gcagagaaaa ggctggtgga gattgtaaat tatgtgaaag tgcagtgctc cacctacacc     180
cattttaatg aatcttcgga atcaaaaagc ctcctccgtg cgattgaaag tgccagacag     240
atgagtacca atattaacat ggaaacagaa aacggcggtc agctgagccg ggaatttctg     300
aaaggaaacc tgcagactct ctgggtggat ggtatcattg tactggataa agaaggaaag     360
acggattgtg aatacagcac ggatgaatct cttgccaatg agattacgga gtatctgcaa     420
aaagaaatta tcatggattt tgccggatat gaagaaagat cttattcgga acgttttatt     480
agagaagacg ggtcgcgtat cgacattgca gcctgtgcca gaaaagatgt accgggtatc     540
gttgctgttt attattatac atctccggaa tttgtcagaa actacacact gacgatacag     600
gggcttttaa acggttatag tgttcagaaa gatggaacga ttattgttgc agacaatggg     660
atcgtt                                                                666

<210> SEQ ID NO 50
<211> LENGTH: 456
<212> TYPE: DNA
<213> ORGANISM: Artificial
<220> FEATURE:
<223> OTHER INFORMATION: biomarker

<400> SEQUENCE: 50
cttacccata aggaggaaaa tcatatgaaa gaatttcgaa acaaacttat tgtccatggt      60
ttaatgaaaa tcaatgataa ataccttgtc attaaaagaa gtattatcaa aagaggtaaa     120
ccaaatgtat atcctgaata ttgggatatt cctggaggct ccgtagaaga ctttgaaaca     180
cctgtagaag ctttaattag agaagctaaa gaagaagtta atttagatgt tgaaataaaa     240
caaatcattc atgaagatag taattttgat aaaggtaaaa atacgatgtt tacccgtctt     300
gtttatattt gtactttaaa aaatactact gattatacaa ttcaattaga ttctgaagaa     360
catagtgaat atcgtcttat ttcttcttta gatgaaatgt ctaatgaaaa agttgttcca     420
tttttaatgg atatcttatc taataaaaat ctctaa                               456
```